(12) United States Patent
Bae et al.

(10) Patent No.: US 7,138,274 B2
(45) Date of Patent: Nov. 21, 2006

(54) ADVANCED ORAL POLIOVIRUS VACCINE (ADV-OPV) DEPRIVED OF THE POSSIBILITY OF VACCINE ASSOCIATED PARALYTIC POLIOMYELITIES (VAPP)

(75) Inventors: Yong-Soo Bae, Suwon (KR); Sang-Gu Lee, Daejeon Metropolitan (KR); Hye-Rhan Jeong, Daejeon Metropolitan (KR); Dong-Sung Lee, Daejeon Metropolitan (KR); Ki-Tae Kim, Daejeon Metropolitan (KR); Dae-You Kim, Daejeon Metropolitan (KR)

(73) Assignee: Creagene, Inc., Gyeonggi-do (KR)

( * ) Notice: Subject to any disclaimer, the term of this patent is extended or adjusted under 35 U.S.C. 154(b) by 5 days.

(21) Appl. No.: 10/926,333

(22) Filed: Aug. 26, 2004

(65) Prior Publication Data

US 2006/0045889 A1    Mar. 2, 2006

(51) Int. Cl.
   C12N 15/00     (2006.01)
   A61K 39/00     (2006.01)
   A61K 39/295    (2006.01)
   A61K 39/13     (2006.01)
   C12N 7/00      (2006.01)

(52) U.S. Cl. ............... 435/320.1; 424/185.1; 424/192.1; 424/202.1; 424/217.1

(58) Field of Classification Search ......... 424/217.1, 424/199.1, 205.1; 435/320.1, 91.4, 91.41, 435/235.1, 5, 456, 320
   See application file for complete search history.

(56) References Cited

U.S. PATENT DOCUMENTS 5,965,124 A    10/1999   Feinberg et al. ........ 424/93.21

6,696,289 B1 *  2/2004   Bae et al. ............... 435/320.1
6,780,618 B1 *  8/2004   Lee et al. ................ 435/91.4

OTHER PUBLICATIONS

Ren, R. et al., Transgenic mice expressing a human poliovirus receptor: a new model for poliomyelitis. Cell. Oct. 19, 1990;63(2):353-62.*

Crotty, S. et al., Poliovirus pathogenesis in a new poliovirus receptor transgenic mouse model: age-dependent paralysis and a mucosal route of infection. J Gen Virol. Jul. 2002;83(Pt 7):1707-20.*

"Immnization Schedule, Children; Poliovirus" at http://emedicinehealth.com/articles/11995-5.asp accessed on Monday, Mar. 14, 2005 at 1:30 P.M.*

Delpeyroux, F. et al. Presentation and immunogenicity of the hepatitis B surface antigen and a poliovirus neutralization antigen on mixed empty envelope particles. J virol. May 1988;62(5):1836-9.*

Lee et al, Journal of Virology, Feb. 2002, vol. 76, No. 4, pp. 1649-1662.

Mattion et al, Journal of Virology, Jun. 1994, vol. 68, No. 6, pp. 3925-3933.

* cited by examiner

*Primary Examiner*—James C. Housel
*Assistant Examiner*—M. Franco Salvoza
(74) *Attorney, Agent, or Firm*—Nixon & Vanderhye P.C.

(57) ABSTRACT

The present invention relates to a novel recombinant Sabin type 1 poliovirus vector for the immunogenicity of neutralizing antibody against poliviral infection, which comprises: (a) a genomic nucleotide sequence of a parent Sabin type 1 poliovirus; (b) a nucleotide sequence encoding an additional polioviral cleavage site; and (c) a nucleotide sequence of a conformational epitope encoding a VP1 neutralizing epitope of poliovirus type 2 or 3 and linked to the nucleotide sequence of (b).

15 Claims, 17 Drawing Sheets

(14 of 17 Drawing Sheet(s) Filed in Color)

Fig. 1

```
     735                                                   771
5'-- GTATCATA ATG GGT GCT CAG GTT TCA TCA CAG AAA GT---3'
              M   G   A   Q   V   S   S   Q   K

SstII      HpaI      EagI                     3C
           CCC CGG    GTT AAC   CGG CCG    GCT TTG TTC   CAA
            P   R      V   N     R   P      A   L   F    Q
``` pTZ-18/R

RPS-Vax
(10.4Kbp)

Sabin 1 cDNA

EcoRI
PT7
1
BanI
745 905
1813  PstI
2243  PstI
3417
3520  PstI
BanI
7440
SalI
EcoRI

Fig. 2

Poliovirus genome

```
Vpg    743
 o————[  P1  |  P2  |  P3  ]————AAA3'
```

```
        735              M   G   A   Q   V   S   S   Q   K   771
5'-- GTATCATA ATG GGT GCT CAG GTT TCA TCA CAG AAA GT---3'    Sabin 1

M   G   A   P   R   V   N   R   P   A   L   F   Q   G
5'--- ATG GGT GCT CCC CGG GTT AAC CGG CCG GCT TTG TTC CAA GGT -3'    RPS-Vax
                   SstII    HpaI    EagI                ↑
                                                     3C-protease 680 →    ┌─────────────────┐
   ─────────  │  foreign insert │  ─────────    rec-PV
              └─────────────────┘    ← 814
```

Anti-Lansing antiserum

Anti-Leon antiserum

Sabin type 1 antiserum   Sabin type 2 antiserum   Sabin type 3 antiserum

Fig. 6b

| | 1 | 2 | 3 | 4 |

Human anti-OPV serum

Mouse anti-Mahoney serum

Mouse anti-Lansing serum       VP1 (33 KDa)

Mouse anti-Leon serum

PV2-Peptide antiserum  α-Tag mAb

PV3-Peptide antiserum  α-Tag mAb

Fig. 9

RPS-Vax/PV2-138      RPS-Vax/PV3-138

C   3   6   9   12        C   3   6   9   12

A. Inoculation route

VP1 (33 KDa)

B. Inoculation dose

VP1 (33 KDa)

C. Immunogenicity

VP1 (33 KDa)

Neutralizing Ab titer to Mahoney

B

Neutralizing Ab titer to Lansing

C

Neutralizing Ab titer to Leon

Fig. 12a

OPV-OPV-OPV Program rOPV-rOPV-rOPV Program

Fig. 12c rOPV-IPV-IPV Program

SEQUENCE LISTING

<160> NUMBER OF SEQ ID NOS: 8

<210> SEQ ID NO 1
<211> LENGTH: 300
<212> TYPE: PRT
<213> ORGANISM: Poliovirus Type 2 (Lancing)

<400> SEQUENCE: 1

```
Gly Leu Gly Asp Leu Ile Glu Gly Val Val Glu Gly Val Thr Arg Asn
  1               5                  10                  15

Ala Leu Thr Pro Leu Thr Pro Ala Asn Asn Leu Pro Asp Thr Gln Ser
             20                  25                  30

Ser Gly Pro Ala His Ser Lys Glu Thr Pro Ala Leu Thr Ala Val Glu
         35                  40                  45

Thr Gly Ala Thr Asn Pro Leu Val Pro Ser Asp Thr Val Gln Thr Arg
     50                  55                  60

His Val Ile Gln Lys Arg Thr Arg Ser Glu Ser Thr Val Glu Ser Phe
 65                  70                  75                  80

Phe Ala Arg Gly Ala Cys Val Ala Ile Ile Glu Val Asp Asn Asp Ala
                 85                  90                  95

Pro Thr Lys Arg Ala Ser Lys Leu Phe Ser Val Trp Lys Ile Thr Tyr
            100                 105                 110

Lys Asp Thr Val Gln Leu Arg Arg Lys Leu Glu Phe Phe Thr Tyr Ser
        115                 120                 125

Arg Phe Asp Met Glu Phe Thr Phe Val Val Thr Ser Asn Tyr Thr Asp
    130                 135                 140

Ala Asn Asn Gly His Ala Leu Asn Gln Val Tyr Gln Ile Met Tyr Ile
145                 150                 155                 160

Pro Pro Gly Ala Pro Ile Pro Gly Lys Trp Asn Asp Tyr Thr Trp Gln
```

-continued

```
                165                 170                 175
Thr Ser Ser Asn Pro Ser Val Phe Tyr Thr Tyr Gly Ala Pro Pro Ala
            180                 185                 190

Arg Ile Ser Val Pro Tyr Val Gly Ile Ala Asn Ala Tyr Ser His Phe
        195                 200                 205

Tyr Asp Gly Phe Ala Lys Val Pro Leu Ala Gly Gln Ala Ser Thr Glu
    210                 215                 220

Gly Asp Ser Leu Tyr Gly Ala Ala Ser Leu Asn Asp Phe Gly Ser Leu
225                 230                 235                 240
Ala Val Arg Val Val Asn Asp His Asn Pro Thr Lys Leu Thr Ser Lys
                245                 250                 255
Ile Arg Val Tyr Met Lys Pro Lys His Val Arg Val Trp Cys Pro Arg
            260                 265                 270

Pro Pro Arg Ala Val Pro Tyr Tyr Gly Pro Gly Val Asp Tyr Lys Asp
        275                 280                 285

Gly Leu Ala Pro Leu Pro Gly Lys Gly Leu Thr Thr
    290                 295                 300

<210> SEQ ID NO 2
<211> LENGTH: 300
<212> TYPE: PRT
<213> ORGANISM: Poliovirus Type 3 (Leon)

<400> SEQUENCE: 2

Gly Ile Glu Asp Leu Ile Ser Glu Val Ala Gln Gly Ala Leu Thr Leu
  1               5                  10                  15

Ser Leu Pro Lys Gln Gln Asp Ser Leu Pro Asp Thr Lys Ala Ser Gly
            20                  25                  30

Pro Ala His Ser Lys Glu Val Pro Ala Leu Thr Ala Val Glu Thr Gly
        35                  40                  45

Ala Thr Asn Pro Leu Ala Pro Ser Asp Thr Val Gln Thr Arg His Val
     50                  55                  60

Val Gln Arg Arg Ser Arg Ser Glu Ser Thr Ile Glu Ser Phe Phe Ala
 65                  70                  75                  80

Arg Gly Ala Cys Val Ala Ile Ile Glu Val Asp Asn Glu Gln Pro Thr
                 85                  90                  95

Thr Arg Ala Gln Lys Leu Phe Ala Met Trp Arg Ile Thr Tyr Lys Asp
            100                 105                 110

Thr Val Gln Leu Arg Arg Lys Leu Glu Phe Phe Thr Tyr Ser Arg Phe
        115                 120                 125

Asp Met Glu Phe Thr Phe Val Val Thr Ala Asn Phe Thr Asn Ala Asn
    130                 135                 140

Asn Gly His Ala Leu Asn Gln Val Tyr Gln Ile Met Tyr Ile Pro Pro
145                 150                 155                 160

Gly Ala Pro Thr Pro Lys Ser Trp Asp Asp Tyr Thr Trp Gln Thr Ser
                165                 170                 175

Ser Asn Pro Ser Ile Phe Tyr Thr Tyr Gly Ala Ala Pro Ala Arg Ile
            180                 185                 190

Ser Val Pro Tyr Val Gly Leu Ala Asn Ala Tyr Ser His Phe Tyr Asp
        195                 200                 205

Gly Phe Ala Lys Val Pro Leu Lys Thr Asp Ala Asn Asp Gln Ile Gly
    210                 215                 220

Asp Ser Leu Tyr Ser Ala Met Thr Val Asp Asp Phe Gly Val Leu Ala
225                 230                 235                 240
```

-continued

```
Val Arg Val Val Asn Asp His Asn Pro Thr Lys Val Thr Ser Lys Val
                245                 250                 255

Arg Ile Tyr Met Lys Pro Lys His Val Arg Val Trp Cys Pro Arg Pro
            260                 265                 270

Pro Arg Ala Val Pro Tyr Tyr Gly Pro Gly Val Asp Tyr Lys Asn Asn
        275                 280                 285

Leu Asp Pro Leu Ser Glu Lys Gly Leu Thr Thr Tyr
    290                 295                 300

<210> SEQ ID NO 3
<211> LENGTH: 8
<212> TYPE: PRT
<213> ORGANISM: Poliovirus Type 2 (Lancing)

<400> SEQUENCE: 3

Glu Val Asp Asn Asp Ala Pro Thr
  1               5

<210> SEQ ID NO 4
<211> LENGTH: 8
<212> TYPE: PRT
<213> ORGANISM: Poliovirus Type 3 (Leon)

<400> SEQUENCE: 4

Asn Glu Gln Pro Thr Thr Arg Ala
  1               5

<210> SEQ ID NO 5
<211> LENGTH: 24
<212> TYPE: DNA
<213> ORGANISM: Poliovirus Type 2 (Lancing)

<400> SEQUENCE: 5
gaagtggata atgatgctcc aaca                                              24

<210> SEQ ID NO 6
<211> LENGTH: 24
<212> TYPE: DNA
<213> ORGANISM: Poliovirus Type 3 (Leon)

<400> SEQUENCE: 6
aatgaacaac caaccacccg ggca                                              24

<210> SEQ ID NO 7
<211> LENGTH: 414
<212> TYPE: DNA
<213> ORGANISM: Poliovirus Type 2 (Lancing)

<400> SEQUENCE: 7
cacgtcatcc aaaagcggac gcggtcggag tctacggttg agtctttctt cgcaagagga      60
gcttgtgtgg ccattattga agtggataat gatgctccaa caaagcgtgc cagtaaatta     120
ttttcagtct ggaagataac ttacaaagac accgttcagt taagacgtaa gttggagttc     180
tttacatatt caaggtttga catggagttc acctttgtgg ttacatccaa ttataccgat     240
gcaaacaatg ggcacgcact aaatcaagtt taccagataa tgtacatacc acctggggca     300
ccgatccctg gcaagtggaa tgattacaca tggcaaacgt catctaaccc atcagtgttt     360
tacacttacg gggcacctcc agctagaata tcagtgccct acgtgggcat tgcc           414

<210> SEQ ID NO 8
<211> LENGTH: 414
```

-continued

<212> TYPE: DNA
<213> ORGANISM: Poliovirus Type 3 (Leon)

<400> SEQUENCE: 8

```
cacgtagtcc aacgacgcag caggtcagag tccacaatag aatcattctt cgcacgcggg      60
gcgtgcgtcg ctattattga ggtggacaat gaacaaccaa ccacccgggc acagaaacta     120
tttgccatgt ggcgcattac atacaaagat acagtgcagt tgcgccgtaa gttggagttt     180
ttcacatact ctcgttttga catggaattc accttcgtgg taaccgccaa cttcaccaac     240
gctaataatg ggcatgcact caaccaggtg taccagataa tgtacatccc cccagggca      300 cccacaccaa agtcatggga cgactacact tggcaaacat cttccaaccc gtccatattt     360
tacacctatg gggctgcccc ggcgcgaatc tcagtgccat acgtggggtt agcc           414
```

ADVANCED ORAL POLIOVIRUS VACCINE (ADV-OPV) DEPRIVED OF THE POSSIBILITY OF VACCINE ASSOCIATED PARALYTIC POLIOMYELITIES (VAPP)

BACKGROUND OF THE INVENTION

1. Field of the Invention

The present invention relates to a novel recombinant Sabin type 1 poliovirus vector, in particular, to a recombinant Sabin type 1 poliovirus vector to induce the generation of neutralizing antibody, a vaccine composition comprising a recombinant poliovirus and a method for immunizing an individual against poliovirus.

2. Description of the Related Art

Recent standards for vaccine development commonly emphasize the mucosal immunity. Several researches for the development of effective mucosal vaccines have been performed as follows:

Firstly, cholera toxin or E. coli endotoxin have been suggested as a kind of mucosal immunogens (Munoz, E. et al., Cholera toxin discriminates between T helper 1 and 2 cells in T cell receptor-mediated activation: role of cAMP in T cell proliferation. J. Exp. Med. 1; 172(1):95–103(1990); Wilson, A. D. et al., Adjuvant action of cholera toxin and pertussis toxin in the induction of IgA antibody response to orally administered antigen. Vaccine 11(2):113–8(1993)). However, since cholera toxin and bacterial endotoxin may induce adverse effects in human, much more intensive studies are required for employing them as an adjuvant for mucosal vaccine developments.

Secondly, a microencapsulation technology in which antigens are encapsulated and administered has been reported (McGhee, J. R. et al., Isotype of anti-SIV responses in infected rhesus macaques and in animals immunized by mucosal routes. AIDS Res. Hum. Retroviruses 8(8):1389 (1992); Marx., P. A. et al., Protection against vaginal SIV transmission with microencapsulated vaccine Science 28;260(5112):1323–7(1993)). However, this approach also has its own limitation to overcome for antigen combinations to achieve appropriate systemic and mucosal immunities.

Thirdly, viruses showing tropisms to the mucosal area via respiratory and digestive organs have been investigated as the most effective approach for induction of mucosal immunity, which are able to induce both cytotoxic T lymphocyte (CTL) and local mucosal immunity (Meitin C. A. et al., Influenza immunization: intranasal live vaccinia recombinant contrasted with parenteral inactivated vaccine Vaccine 9(10):751–6(1991); Offit, P. A. et al., Rotavirus-specific cytotoxic T lymphocyte response of mice after oral inoculation with candidate rotavirus vaccine strains RRV or WC3. J. Infect. Dis. 160(5):783–8(1989); London, S. D. et al., Intraepithelial lymphocytes contain virus-specific, MHC-restricted cytotoxic cell precursors after gut mucosal immunization with reovirus serotype 1/Lang. Reg. Immunol. 2(2): 98–102(1989)).

Therefore, it was highly recommended to construct a viral vector with mucosal tissue-tropic viruses, resulting in the development of recombinant mucosal vaccines by integrating various viral subgenomes into the viral vector.

In this connection, much effort has been recently made to develop non-toxic viral vectors having higher potential for the induction of mucosal immunity. In particular, the development of vaccines using poliovirus has been extensively studied.

Studies for the development of poliovirus as a vector can be classified into 3 categories: (a) epitope substitution; (b) construction of defective minireplicon; and (c) autoprocessing recombinant vector (R. Andino, Science 265:1448–451 (1994)); N. M. Mattion J. Virol. 68:3925–3933(1994); and Vaccine 95:293–297(1995)). In the third category, R. Andino et al. used wild type of poliovirus (type 1 Mahoney strain) and N. M. Mattion used type 3 Sabin for the development of viral vector, reporting their experimental results.

The approaches proposed by R. Andino and Mattion are considered the most promising. However, Sabin type 3 as well as Mahoney strain has its own limitation for the safety reasons mediated by back mutation.

Sabin developed poliovirus vaccine in 1963, which proliferates only in small intestine without neurotropism, and induces long-lasting mucosal immunity. It does not cause poliomyelitis even in the high titers. Among the Sabin strains, the Sabin 1 has been approved for its safety. During the last 40 years none of the case of vaccine-associated paralytic poliomyelitis (VAPP) has been reported in association with Sabin 1.

In these regards, the present inventors have developed recombinant live vaccine vectors by manipulating a genome of Sabin type 1, named "RPS-Vax" (see Korean Pat. Appln. No. 1997-37812). In addition, the present inventors have constructed Sabin type 1-based recombinant poliovirus vectors by inserting p24 gene of HIV-1, env gene of HIV-1 and core gene of HCV into the RPS-Vax vector system (see WO 99/7859).

The RPS-Vax-derived recombinant live vaccines are expected to take advantages of Sabin I vaccine strain, such as safety, oral administration, low cost and its mucosal immunogenicity.

Inactivated polio vaccine (IPV; Salk) was developed in 1953 as the first polio vaccine. The IPV was made of formalin-inactivated wild type polioviruses of types 1, 2 and 3. Recent inactivated polio vaccines, produced by culturing in human diploid cells or Vero cells, are much improved for their efficacy. They exhibit considerable preventive immunity even by twice inoculations. In addition, it has been suggested that theses vaccines could elicit the same seroconversion rate as that of oral polio vaccines (OPV) through thrice-basic inoculation. Although the IPVs are much more safe than oral live vaccines, they have some serious shortcomings: (a) demand of much higher does for immunization than live vaccines ($10^{12}$ pfu/human vs. $5-10 \times 10^5$ pfu/human); (b) needle injection; (c) no held immunity; and (d) no musoal immunogenicity.

OPV has been one of the most successful vaccine programs during the last half of the 20th century. The incidence of poliomyelitis was sharply reduced by OPV development since 1963, and recently expected to be eradicated in the near future all over the world. The OPV has been produced in a form of cocktail comprising attenuated vaccine strains of Sabin types 1, 2 and 3. Recently, however, vaccine associated paralytic poliomyelitis (VAPP) has been reported in line with OPV vaccination in USA. Because of the VAPP by OPV, several developed countries, starting with USA and Germany since the year of 1999, have inclined to use IPVs rather than OPV.

Nevertheless, many underdeveloped countries still have lots of incidences of poliomyelitis in Southeast Asia and Africa. Even though very safe, IPV is not enough to keep these peoples from the poliomyelitis for its own limitations of weak immunogenicity, expenses and no capacity for mucosal immunity. Therefore, it is highly recommended to develop a safe and effective OPV to replace the conventional OPV.

Although several studies have been made for a long period of time to dispel the adverse effects associated with OPV, there has not yet been provided safe and effective vaccines for replacing conventional OPV vaccine.

Throughout this application, several patents and publications are referenced and citations are provided in parentheses. The disclosure of these patents and publications is incorporated into this application in order to more fully describe this invention and the state of the art to which this invention pertains.

SUMMARY OF THE INVENTION

Under such circumstances of conventional techniques described previously, the present inventors have made intensive researches to develop a safe and effective recombinant oral poliovirus vaccine, which is able to neutralize three different types of wild type polioviruses. The inventors constructed Sabin type 1 poliovirus vector (RPS-Vax) and then developed novel recombinant OPV vaccine candidates by incorporating neutralizing epitope regions of poliovirus type 2 (or type 3) VP1 into RPS-Vax vector system. The inventors' recombinant OPV has been found very effective for the induction of the neutralizing antibody against poliovirus type 2 (or 3) as well as poliovirus type 1, thereby providing safe and effective vaccine programs against poliovirus infection.

Accordingly, it is an object of this invention to provide a recombinant Sabin type 1 poliovirus vector.

It is another object of this invention to provide a vaccine composition of recombinant OPV comprising a recombinant Sabin type 1 poliovirus.

It is still another object of this invention to provide a method for immunizing an individual against wild types of polioviruses.

It is further object of this invention to provide a method for testing a prevention efficacy induced by a recombinant Sabin strain against polioviral infection.

It is further object of this invention to provide a method for testing a prevention immunity induced by a recombinant OPV against polioviral infection.

Other objects and advantages of the present invention will become apparent from the detailed description to follow taken in conjunction with the appended claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 represents a genetic map and cloning site of Sabin 1-based RPS-Vax vector used for constructing a recombinant poliovirus of this invention. RPS-Vax genome contains multiple cloning site (MCS) and 3C-protease cutting site at the N-terminal end of the long polyprotein.

FIG. 2 shows a cloning scheme of foreign insert into RPS-Vax system to produce a recombinant poliovirus of this invention. Foreign insert, integrated into the MCS, can be easily detected by RT-PCR with the primer set indicated by arrows.

FIG. 6*a* shows the results of Western blot analysis to test cross-immune responses with antiserum obtained from Tg-PVR mice immunized with poliovirus vaccine strains. M denotes a staining marker and lanes 1–3 represent HeLa/Sabin type 1 infection lysate, HeLa/Sabin type 2 infection lysate and HeLa/Sabin type 3 infection lysate.

FIG. 6*b* shows the results of Western blot analysis to test cross-immune responses with antiserum obtained from Tg-PVR mice immunized with each of 3 different wild type polioviruses. Lane 1, HeLa/Mahoney infection lysate; lane 2, HeLa/W-2 infection lysate; lane 3, HeLa/Lansing infection lysate; and lane 4, HeLa/Leon infection lysate.

FIG. 9 demonstrates the genetic stability and expression of RPS-Vax/PV2-138 and RPS-Vax/PV3-138, preferable embodiments of this invention, which were analyzed by RT-PCR and Western blot. Lane C represents the control HeLa cell lysate infected with RPS-Vax-derived control virus having no insert. Numbers denote passage number. Arrows indicate PCR-amplified insert sequences and expressed proteins.

FIG. 11 shows the titer of neutralizing antibody against Mahoney (panel A), Lansing (panel B) and Leon strains (panel C) in the antiserum obtained from the mice immunized with Sabin type 1 and recombinant viruses RPS-Vax/PV2 and RPS-Vax/PV3. In graph A, bar 1 represents the antiserum from the mice inoculated three times with Sabin type 1, and bars 2 and 3 represent the antisera from mice inoculated first with RPS-Vax virus and then boosted with formalin-inactivated Sabin type 2 once and twice, respectively. Bars 4 and 5 represent the antisera from the mice inoculated with Sabin type 1 and then boosted with inactivated Sabin type 3 once and twice. In graph B, bar 1 represents the antiserum from the mice inoculated three times with Sabin type 2, bar 2 represents the antiserum from mice inoculated with RPS-Vax control virus and then boosted twice with inactivated Sabin type 2, bar 3 represents the antiserum from the mice inoculated with RPS-Vax/PV2-110 recombinant virus and then boosted twice with inactivated Sabin type 2, bar 4 represents the antiserum from the mice inoculated with RPS-Vax/PV2-110-Tag recombinant virus and then boosted twice with inactivated Sabin type 2, bar 5 represents the antiserum from the mice inoculated with RPS-Vax/PV2-138 recombinant virus and then boosted twice with inactivated Sabin type 2, and bar 6 corresponds to the antiserum from the mice inoculated with RPS-Vax/PV2-138-PTD recombinant virus and then boosted twice with inactivated Sabin type 2. In graph C, bar 1 corresponds to the antiserum from the mice immunized three times with Sabin type 3, bar 2 corresponds to the antiserum from the mice immunized with RPS-Vax virus and then boosted twice with inactivated Sabin type 3, bar 3 corresponds to the antiserum prepared from the mice inoculated with RPS-Vax/PV3-110 recombinant virus and then boosted twice with inactivated Sabin type 3, bar 4 corresponds to the antiserum obtained from the mice inoculated with RPS-Vax/PV3-110-Tag recombinant virus and then boosted twice with inactivated Sabin type 3, bar 5 corresponds to the antiserum obtained from the mice inoculated with RPS-Vax/PV3-138 recombinant virus and then boosted twice with inactivated Sabin type 3, and bar 6 corresponds to the antiserum obtained from the mice inoculated with RPS-Vax/PV3-138-PTD recombinant virus and then boosted twice with inactivated Sabin type 2.

FIGS. 12a–12c represent the results of in vitro neutralizing assay for OPV-OPV-OPV program, IPV-IPV-IPV program and rOPV-IPV-IPV program.

DETAILED DESCRIPTION OF THIS INVENTION

Figure 3:
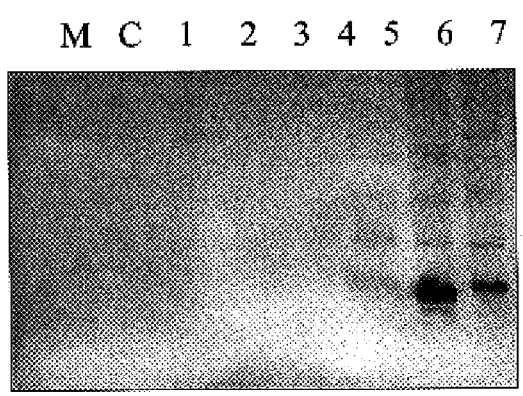
FIG. 3 shows the results of Western blot analysis using anti-Lansing antiserum (panel A) or anti-Leon antiserum (panel B) obtained from Tg-PVR mouse. Lanes M, C, 1, 2, 3, 4, 5, 6 and 7 represent NEB prestained marker, 1 μg control BSA, PV2-NEP (neutralizing epitope peptide)-BSA conjugate, PV3-NEP-BSA conjugate, PV2-NEP-ovalbumin conjugate, PV3-NEP-ovalbumin conjugate, PV2-NEP-ovalbumin conjugate, PV3-NEP-ovalbumin conjugate, HeLa/Mahoney lysate, HeLa/Lansing lysate and HeLa/Leon lysate, respectively.
Figure 3:
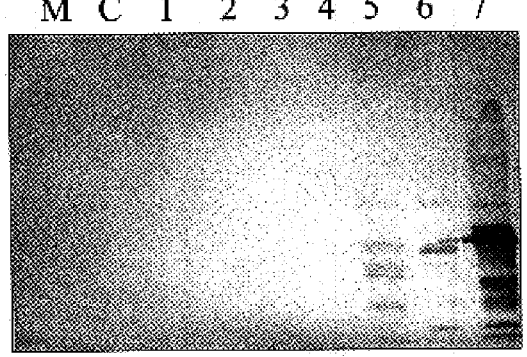

In one aspect of this invention, there is provided a recombinant Sabin type 1 poliovirus vector, which comprises: (a) a genomic nucleotide sequence of a parent Sabin type 1 poliovirus; (b) a nucleotide sequence encoding an additional poliviral cleavage site; and (c) a nucleotide sequence of a conformational epitope encoding a VP1 neutralizing epitope of poliovirus type 2 or 3 and linked to the nucleotide sequence of (b).

It is believed unnecessary to develop a CTL (cytotoxic T lymphocyte) vaccine against poliovirus for its short life cycle (approximately 12 hr). Instead, a vaccine for inducing a neutralizing antibody to block the binding of poliovirus to its host cell is promising for the prevention of polio. Therefore, the present inventors have focused on the development of recombinant polioviruses appropriate for the induction of a neutralizing antibody.

The icosahedral capsid, a structural protein of poliovirus, is fabricated with 60 copies of capsomers consisting of VP1, VP2, VP3 and VP4. Through a pocket structure called "canyon" in the capsid, poliovirus binds to the poliovirus receptor of host cells and introduced into host cells by the receptor-mediated endocytosis.

While the location and conformation of neutralizing epitopes of poliovirus are very similar in 3 serotypes, they have each different antiserotype due to the difference of their amino acid sequences. A neutralizing antibody induced by recombinant polioviruses derived from vectors of this invention is a conformational antibody to recognize a specific conformation induced by B cell epitope, binding to the canyon region to block the binding of polioviruses to the PVR (poliovirus receptor) of host cells. For inducing the generation of neutralizing antibody, the vector of the present invention comprises a nucleotide sequence of a conformational epitope encoding a neutralizing epitope.

The term "conformational epitope" used herein refers to an epitope satisfying the following criteria: (a) having a sequence corresponding to the neutralizing epitope in the full sequence of poliovirus VP1; (b) capable of forming a domain structure of neutralizing epitope in the tertiary structure folded by the VP1 full sequence; (c) having approximately 150 amino acid residues in size; (d) exhibiting antigeicity; and (e) capable of inducing antibodies to bind to the canyon region of polioviral capsid.

Among the criteria for the conformational epitope, the limitation of size is set by referring to the most preferable size of foreign protein in Sabin vectors, which has also been elucidated by the present inventors (Korean Pat. Appln. No. 2001-6229; and Lee et al., J. Virol 76:1649–1662(2002)). The size larger than the limited size will give rise to serious problem in terms of genetic stability of DNA sequence encoding conformational epitope. It is essential that the conformational epitope have the capability to form a domain structure of neutralizing epitope for inducing the generation of neutralizing antibody. The present inventors have designed selected a sequence in VP1 sequence capable of form the domain structure by a molecular modeling approach.

The present vector follows the strategies using additional cleavage sites for polioviral proteases as disclosed in WO 99/07859, Korean Pat. Appln. No. 2001-6229 and U.S. Pat. No. 5,965,124, which are incorporated herein by references.

According to a preferred embodiment, the additional polioviral cleavage site is a cleavage site for poliovirus 3C, 3D or 2A protease, more preferably, 3C or 2A protease and most preferably, 3C protease.

According to the present invention, the additional polioviral cleavage site is inserted at a location in the genome of the parent Sabin type 1 poliovirus such that it does not disrupt a polioviral sequence necessary for polioviral replication and proliferation. For example, the artificial (additional) proteolytic cleavage site is inserted at the junction between the first and second amino acid residues of N-terminal, VP0 and VP3, VP3 and VP1, VP1 and 2Apro, 2Apro and 2B, 2B and 2C, 2C and 3A, 3A and Vpg, Vpg and 3Cpro, or 3Cpro and 3Dpol. Preferably, the additional cleavage site is formed at the junction between the first and second amino acid residues of N-terminal, VP1 and 2Apro, 2Apro and 2B, 2C and 3A or Vpg and 3Cpro, most preferably, between the first and second amino acid residues of N-terminal.

The nucleotide sequence encoding a neutralizing epitope inserted additionally in Sabin type 1-based vector of this invention may be varied unless it does not interfere with replication and proliferation of Sabin type 1 poliovirus.

In addition, it is preferred that the nucleotide sequence encoding a neutralizing epitope to exhibit a remarkable genetic stability is selected. The term used herein "genetic stability" refers to that the insert sequence integrated into a recombinant poliovirus is stably maintained in insert-containing recombinant poliovirus during consecutive passage, generally, at least $4^{th}$ passage, preferably, at least $8^{th}$ passage, more preferably, at least 10$^{th}$ passage and most preferably, at least 12$^{th}$ passage. Such genetic stability is significantly highlighted in the senses that the recombinant poliovirus vector of this invention play is used for vaccination. Only the nucleotide sequence showing genetic stability can induce immune responses with substantially identical level in several passages.

In this context, the present inventors have reported the advanced approaches to improve genetic stability of insert nucleotide sequences (Korean Pat. Appln. No. 2001-6229; and Lee et al., *J. Virol.* 76:1649–1662(2002)). According to our previous studies, the genetic stability of the insert nucleotide sequence is remarkably increased where it has the size of less than about 450 bp, lacks local A/T rich regions and shows even distribution of G/C content throughout the overall sequence. The nucleotide sequences complying with the requirements for genetic stability may be prepared by selecting from a natural-occurring nucleotide sequence or mutagenesis. The mutagenesis may be carried out in accordance with processes of site-directed mutagenesis or cassette mutagenesis. In addition, the nucleotide sequences with improved genetic stability may be prepared according to the ligation-free PCR process suggested by the present inventors (Korean Pat. Appln. No. 2001-6229; and Lee et al., *J. Virol.* 76:1649–1662(2002)).

According to the present invention, the nucleotide sequence of the conformational epitope comprises a sequence encoding the VP1 neutralizing epitope (SEQ ID NO:3 for poliovirus type 2; and SEQ ID NO:4 for poliovirus type 3). Most preferably, the nucleotide sequence encoding the VP1 neutralizing epitope comprises a sequence indicated in SEQ ID NO:5 (for poliovirus type 2) or SEQ ID NO:6 (for poliovirus type 3).

According to a preferred embodiment, the nucleotide sequence of the conformational epitope encoding the VP1 neutralizing epitope of poliovirus type 2 comprises a nucleotide sequence encoding the amino acid 65–202 of SEQ ID NO:1. Most preferably, the nucleotide sequence comprises a sequence of SEQ ID NO:7. The nucleotide sequence encoding amino acids 65–202 of the VP1 epitope may be modified for improving genetic stability as described previously, so long as the polypeptide encoded is capable of inducing the generation of conformational (neutralizing) antibody. In addition, it could be understood based on the general state of the art that other equivalent sequences to the amino acid 65–202 of SEQ ID NO:1 are covered by the present invention. For example, some deletions, insertions and substitutions in the amino acid 65–202 of SEQ ID NO:1 are covered by the present invention, unless such mutation abolishes the potency to induce the generation of conformational (neutralizing) antibody.

According to a preferred embodiment, the nucleotide sequence of the conformational epitope encoding the VP1 neutralizing epitope of poliovirus type 3 comprises a nucleotide sequence encoding the amino acid 63–200 of SEQ ID NO:2. Most preferably, the nucleotide sequence comprises a sequence of SEQ ID NO:8. The nucleotide sequence encoding amino acids 63–200 of the VP1 epitope may be modified for improving genetic stability as described previously, so long as the polypeptide encoded is capable of inducing the generation of conformational (neutralizing) antibody. In addition, it could be understood based on the general state of the art that other equivalent sequences to the amino acid 63–200 of SEQ ID NO:2 are covered by the present invention. For example, some deletions, insertions and substitutions in the amino acid 63–200 of SEQ ID NO:2 are covered by the present invention, unless such mutation abolishes the potency to induce the generation of conformational (neutralizing) antibody.

The amino acid sequence as set forth in SEQ ID NO:1 corresponds to VP1 of poliovirus type 2 (Lansing) and that as set forth in SEQ ID NO:2 corresponds to VP1 of poliovirus type 3 (Leon).

In a preferred embodiment of this invention, the backbone of Sabin type 1 recombinant vector of this invention is originated from the Sabin type 1 recombinant vector developed by the present inventors (Korean Pat. Appln. No. 1998-32198; and WO 99/7859), a specific example of which is illustratively represented in FIG. 1.

The Sabin type 1 recombinant vector of this invention for inducing the generation of neutralizing antibody has the capacity of inducing the generation of neutralizing antibody against poliovirus type 1 (Mahoney), because it has a genome sequence of Sabin type 1, and additionally has the capacity of inducing the generation of neutralizing antibody against poliovirus type 2 (Lansing) and 3 (Leon), because it further carries a nucleotide sequence of a conformational epitope encoding a VP1 neutralizing epitope of poliovirus type 2 or 3.

In another aspect of this invention, there is provided a vaccine composition comprising (a) a recombinant Sabin type 1 poliovirus derived from the recombinant Sabin type 1 poliovirus vector discussed hereinabove and (b) a pharmaceutically acceptable carrier.

Since the present vaccine composition comprises, in principle, the Sabin type 1 recombinant vector described above, the common descriptions between them are omitted in order to avoid undue redundancy leading to the complexity of this specification.

The phrase "a recombinant Sabin type 1 poliovirus derived from the recombinant Sabin type 1 poliovirus vector" refers to a recombinant Sabin type 1 poliovirus prepared by using the recombinant Sabin type 1 poliovirus vector of this invention. For example, a RNA transcript is produced by using recombinant Sabin type 1 poliovirus vector of this invention in accordance with various techniques, e.g., in vitro transcription and then tranfected into host cells (e.g., human cells such as HeLa cell) to produce a recombinant Sabin type 1 poliovirus. The prepared recombinant Sabin type 1 polioviruses comprise the nucleotide sequence encoding conformational epitope to contribute to neutralization.

The vaccine composition of this invention is able to induce the generation of neutralizing antibody and the neutralized antibody generated binds to the canyon structure of polioviral capsid to interrupt the interaction between PVR of host cells and the canyon structure, thereby resulting in preventing the infection of poliovirus.

It is notable that recombinant poliovirus live vaccines to induce the generation of neutralizing antibody have not yet developed. The recombinant Sabin type 1 poliovirus used in this vaccine carries neutralizing epitope(s) of wild type poliovirus type 2 and/or 3 and the neutralizing epitopes are designed to maintain their inherent conformation in the whole VP1 protein, conferring the prevention potency against all types (1, 2 and 3) of poliovirus.

According to a preferred embodiment, the recombinant Sabin type 1 poliovirus is a combination of (i) a recombinant Sabin type 1 poliovirus comprising the nucleotide sequence of the conformational epitope encoding the VP1 neutralizing epitope of poliovirus type 2; and (ii) a recombinant Sabin type 1 poliovirus comprising the nucleotide sequence of the conformational epitope encoding the VP1 neutralizing epitope of poliovirus type 3. Where this combination is administered as a vaccine, the generation of neutralizing antibody against each of poliovirus type 1, 2 and 3 can be induced.

The pharmaceutically acceptable carrier may be conventional one for formulation, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxy benzoate, propylhydroxy benzoate, talc, stearic acid, magnesium and mineral oil, but not limited to. The vaccine compositions of this invention, further may contain wetting agent, sweetening agent, emulsifying agent, suspending agent, preservatives, flavors, perfumes, lubricating agent, or mixtures of these substances. For example, it is preferred that the chimeric poliovirus comprised in the vaccine composition may be formulated with $MgCl_2$, sucrose and phosphate for its stabilizing effect. The pharmaceutically acceptable carriers and formulations are found in *Remington's Pharmaceutical Sciences* ($19^{th}$ ed., 1995).

The vaccine compositions of this invention may be administered orally or parenterally. The oral administration is the most preferable mode for the present vaccines.

The correct dosage of the vaccine compositions of this invention will vary according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this vaccine compositions. According to a preferred embodiment, the oral dosage for human host comprises an amount of from $2\times10^5$–$2\times10^7$ $TCID_{50}$, more preferably, $1\times10^6$–$1\times10^7$ $TCID_{50}$.

According to the conventional techniques known to those skilled in the art, the vaccine compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

The most striking feature of the present vaccine composition is to use the recombinant Sabin type 1 poliovirus carrying a nucleotide sequence coding for conformational epitope capable of inducing the generation of neutralizing antibody. Since the recombinant Sabin type 1 poliovirus used in this vaccine carries a nucleotide sequence encoding the conformational epitope(s) derived from VP1 of wild type poliovirus type 2 and/or 3 as well as a genome sequence of Sabin type 1, it can give rise to the prevention potency against each serotype of poliovirus.

In still another aspect of this invention, there is provided a method for immunizing an individual against poliovirus, which comprises administering to the individual the vaccine composition comprising (i) a recombinant Sabin type 1 poliovirus derived from the recombinant Sabin type 1 poliovirus vector described previously and (ii) a pharmaceutically acceptable carrier.

Since the present method uses the present vaccine composition described herein, the common descriptions between them are omitted in order to avoid undue redundancy leading to the complexity of this specification.

According to a preferred embodiment of this invention, the recombinant Sabin type 1 poliovirus is a combination of (i) a recombinant Sabin type 1 poliovirus comprising the nucleotide sequence of the conformational epitope encoding the VP1 neutralizing epitope of poliovirus type 2; and (ii) a recombinant Sabin type 1 poliovirus comprising the nucleotide sequence of the conformational epitope encoding the VP1 neutralizing epitope of poliovirus type 3. Where this combination is administered, the generation of neutralizing antibody against each of poliovirus type 1, 2 and 3 can be induced.

It is preferred that the present method further comprises the step of boosting the individual by administering into the individual an inactivated polio vaccine (IPV) comprised of inactivated Sabin type 1, 2 and 3 polioviruses. Alternatively, the present method further comprises boosting the individual by administering into the individual an inactivated polio vaccine (IPV) comprised of inactivated Sabin type 2 and 3 polioviruses. More preferably, the boosting is carried out twice. The inactivated polio vaccine is used to intend to dispel the occurrence of VAPP (vaccine associated paralytic poliomyelitis).

Accordingly, the most preferable prevention program against poliovirus infection comprises the steps of:

(a) inoculating a combination of (i) a recombinant Sabin type 1 poliovirus comprising the nucleotide sequence of the conformational epitope encoding the VP1 neutralizing epitope of poliovirus type 2; and (ii) a recombinant Sabin type 1 poliovirus comprising the nucleotide sequence of the conformational epitope encoding the VP1 neutralizing epitope of poliovirus type 3;

(b) performing the primary boosting with IPV; and (c) performing the secondary boosting with IPV.

The present immunization process against poliovirus is prominently advantageous in a neutralizing reaction among various immune responses, providing a promising approach to effectively prevent the infection of poliovirus.

In further aspect of this invention, there is provided a method for testing a prevention efficacy of a recombinant Sabin poliovirus against polioviral infection, which comprises the steps of: (a) inoculating the recombinant Sabin poliovirus to be tested into a transgenic mouse harboring a gene of poliovirus receptor; (b) challenging said transgenic mouse with the wild type of poliovirus; and (c) evaluating the development of poliomyelitis or the occurrence of death in said transgenic mouse.

There has not been yet provided the animal model to test the prevention efficacy of vaccine strains, inter alia, the prevention potency through the interference of the interaction between PVR and poliovirus. In this regard, the present animal model takes a giant step toward the evaluation of the prevention efficacy of recombinant poliovirus vaccine strains.

The instant evaluation employs a transgenic mouse harboring a gene of human poliovirus receptor (PVR), a specific example of which is the Tg-mouse prepared by introducing human PVR gene into ICR mouse as discussed in Examples (see Racaniello V. R. et al., Transgenic mice and the pathogenesis of poliomyelitis, *Arch. Virol. Suppl.* 9:79–86(1994); Koike S. et al., Characterization of three different transgenic mouse lines that carry human poliovirus receptor gene-influence of the transgene expression on pathogenesis, *Arch. Virol.* 139(3–4):351–63(1994); Dragunsky E. et al., Transgenic PVR Tg-1 mice for testing of poliovirus type 3 neurovirulence: comparison with monkey test. *Biologicals.* 21(3):233–7(1993); Racaniello V. R. et al., Poliovirus attenuation and pathogenesis in a transgenic mouse model for poliomyelitis, *Dev. Biol. Stand.* 78:109–16(1993); Ren R. et al., Human poliovirus receptor gene expression and poliovirus tissue tropism in transgenic mice, *J. Virol.* 66(1):

296–304(1992); Ren R. B. et al., Transgenic mice expressing a human poliovirus receptor: a new model for poliomyelitis, *Cell* 19;63(2):353–62(1990)). The transgenic mouse is vulnerable to human poliovirus infection and therefore serves as a host for poliovirus.

A recombinant Sabin strain to be tested in accordance with the present method may include any conventional Sabin strain, preferably, Sabin strains having the backbone developed by the present inventors as represented in FIG. 1. Since the recombinant Sabin strains developed by the present inventors exhibit no cross immunity between serotype in Tg-PVR mouse, it becomes very advantageous in testing serotype-specific immune reaction.

In the instant testing process, the inoculation may be performed by various methods and intracerebral or intramuscular injection is very effective in terms of the potency to induce antibody formation. In addition, it is advantageous that the challenging is performed by intracerebral or intramuscular injection. More preferably, the inoculation and challenging is performed by intramuscular injection in the senses that the injection method is convenient and makes the deviation between repetitive inoculations (or challenging) minimized.

Preferably, the dose of the recombinant Sabin poliovirus inoculated ranges from $1\times10^5$ to $5\times10^7$ $TCID_{50}$, more preferably, $2\times10^5$–$2\times10^7$ $TCID_{50}$, most preferably, about $1\times10^7$ $TCID_{50}$. It is preferred that the dose of wild type poliovirus for challenging ranges from $1\times10^5$ to $5\times10^7$ $TCID_{50}$, more preferably, $2\times10^5$–$2\times10^7$ $TCID_{50}$, most preferably, about $1\times10^7$ $TCID_{50}$.

The transgenic mouse used in the instant testing method exhibits both no cross immunity and cross prevention between serotypes of poliovirus to show no non-specific immune responses, so that it enables to test the prevention efficacy against poliovirus by using animals, providing environments similar to human.

Consequently, the present testing process using animal models makes it possible to conveniently select vaccine strains in shorter period of time.

The following specific examples are intended to be illustrative of the invention and should not be construed as limiting the scope of the invention as defined by appended claims.

EXAMPLES

Materials

1. Plasmid and *E. coli* Strain

The poliovirus Sabin 1 cDNA in RPS-Vax vector (Accession No. KCTC 0365BP, Deposition ID: pTZ-PVS-3m) constructed according to proposed by Jung, H. and Y.-S. Bae (*J. Biochem. Mol. Biol.* 31:432–443(1998)) was used. The cDNA has a 30-bp polylinker containing an artificial cleavage site for $3C^{pro}$(AXXQ/G) and a multiple cloning site (SstII, HpaI and EagI restriction sites) (see FIG. 1). PGEM-T easy vector (Promega) was used for cloning PCR products and sequencing. *E. coli* JM 109 (Stratagene) was used because it shows slow proliferation rate and could amplify stably large sized plasmids (11 kb). LB media (1% Bacto tryptone, 1% yeast extract, 0.5% NaCl; Difco) was used and ampicillin (50 μg/ml) was used as a selective marker. PWO enzyme (Roche) having proof-reading activity was used for PCR amplification of antigen gene. For plasmid isolation, Wizard mini prep kit (Promega) with little RNA contamination was used.

2. Virus and Cell Line

For obtaining poliovirus Sabin type 1, recombinant RNAs prepared by in vitro transcription of PTZ-PVS plasmid using T7 RNA polymerase were transfected into HeLa cells according to a DEAE-dextran procedure (Van der Welf et al., *PNAS* 83:2330–2334(1986)). POLIOVAX (Green Cross Company, Korea) was infected into HeLa cells and a single plaque formed thus was isolated for preparing Sabin types 2 and 3. Poliovirus type 1, Mahoney strain was prepared by transfecting into HeLa cells pVS(1)IC-0(T) kindly provided by Dr. A. Nomoto (Institute of Medical Science, The University of Tokyo, Minato-ku, Japan). The wild type 2:W-2 (cat#. VR-301, attenuated from the TN strain but neurovirulence in Tg-PVR mouse), Lansing (cat#: VR-1002) and type 3:Leon (cat#. VR-62, VR-1004) were purchased from ATCC. Monkey serum for each virus was also purchased from ATCC. HeLa cells (HeLa S3 from ATCC) employed for poliovirus propagation and in vitro neutralization assay were cultured in DMEM (GiBcoBRL) containing 10% FBS (GiBcoBRL) under atmosphere of 5% $CO_2$ at 37° C. For the poliovirus propagation in animal test, reduced serum media (OPTI-MEM I: GiBcoBRL) was used.

3. Transgenic Mice

Human poliovirus receptor-transgenic (ICR-PVR-Tg21) mice (Koike, S., C. Taya, T. Kurata, S. Abe, I. Ise, H. Yonekawa, and A. Nomoto. 1991. Transgenic mice susceptible to poliovirus. *Proc. Natl. Acad. Sci. USA* 88:951–955) were kindly provided by Dr. A. Nomoto, University of Tokyo, Japan. These mice were bred and maintained in the Animal Resources Center at the Korea Research Institute of Bioscience and Bioengineering under specific pathogen-free conditions. The Tg-PVR mice harboring stably PCR gene confirmed by PCR were used for experiments. BALB/c mice for antibody production were obtained from the Korean Research Institute of Chemical Technology.

4. Epitope Peptides and Antiserum (1) Serotype Specificity of Poliovirus Antiserum Tg-PVR mice 4 weeks old were inoculated intramuscularly with $5\times10^6$ $TCID_{50}$ of wild type 2: Lansing and wild type 3:Leon and a blood sample was then taken from the vein behind the eye of mice to collect antiserum at the time of the occurrence of paralysis associated with poliomyelitis (3–7 days after inoculation). Antiserums against Sabin types 1, 2 and 3 were obtained 4 weeks after the inoculation performed as described previously. Antiserums obtained were used in Western blotting analysis and in vitro neutralizing assay.

(2) Peptide-Induced Antibody

The peptides consisting of 20 amino acid residues were selected in neutralizing epitope (major antigenic site 1) of the wild types of poliovirus types 2 and 3 and their C-terminal was added with a cysteine residue for conjugation. The peptides consisting of 21 amino acid residues were synthesized in a free form or conjugated form to BSA or ovalbumin for enhancing antigenicity (PEPTRON, Inc., Korea). The synthesized peptides were electrophoresed on 12% SDS-PAGE for confirming conjugation and quantification. The amino acid sequences of peptides synthesized are as follows:

PV2-NEP (neutralizing eptiopte peptide): Lansing VP1(92-111 a.a)

N'-A I I E V D N D A P T K R A S K L F S V C-C'

PV3-NEP: Leon VP1 (92-111 a.a)

N'-I E V D N E Q P T T R A Q K L F A M W R C-C'

50 µg of each BSA-conjugated peptide were mixed with complete adjuvant (cat#:F-5881, SIGMA) at a volume ratio of 1:1 and mixed thoroughly with an ultrasonicator. BALB/c mouse 4 weeks old was subject to the first immunization with the resultant antigen via subcutaneous route. An equal amount of the peptide were mixed with incomplete adjuvant (cat#:F-5506, SIGMA) and for the second immunization the resultant was injected subcutaneously or intraperitonealry 2 week after the first immunization. The third and fourth immunization were performed at the interval of 9 days–2 weeks according to the same procedures as described above. After 5 days of the final injection, antiserum was taken from the vein behind of the eye.

Methods

1. Cloning of Epitope Genes into RPX-Vax Vector

The DNA sequences coding for the VP1 epitopes of poliovirus type 2:W-2 and Lansing, and type 3: Leon were inserted into RPS-Vax system to prepare RPS/PV2 and RPS/PV3. In addition, chimera epitope prepared by combining each VP1 epitope of poliovirus types 2 and 3 was inserted into RPS-Vax system. The chimeric viruses obtained from the recombinant RPS-Vax vectors were analyzed in view of proliferation rate and genetic stability of insert sequence during passage in order to characterize properties of vaccine candidates. FIG. 2 show schematically represents cloning procedures into RPS-Vax vector.

2. In Vitro Transcription

The RPS-Vax plasmids containing insert sequence were linearized with SalI (NEB) and purified by extraction three times with phenol-chloroform, followed by ethanol precipitation to minimize the contamination of RNase. One microgram of linearized plasmid DNA was transcribed in vitro with 5 U/µl T7 RNA polymerase (NEB) in the reaction buffer (40 mM Tris-HCl, pH 8.0, 8 mM $MgCl_2$, 2 mM spermidine, 25 mM NaCl, 5 mM DTT, 1 U/µl RNasin, 2 mM dNTP) for 30 min at 37° C. The resultant was purified several times by extraction with phenol-chloroform and precipitated with ethanol to obtain recombinant RNA transcripts.

3. Transfection into Animal Cells

The RNA transcripts were transfected into HeLa cells by a DEAE-dextran procedure (Van der Welf et al., *PNAS* 83:2330–2334(1986)). 0.2 ml of RNAs (1–2 µg) was mixed into an equal volume of DEAE-dextran (1 mg/Ml in HEPES-buffered saline). The mixture was coated on monolayers of HeLa cells at a confluency of 70%, followed by allowing to stand for 15 min at room temperature. The cells were rinsed twice with PBS and incubated in DMEM containing 10% FCS for 2–3 days. The occurrence of a cytopathic effect was examined.

4. Virus Infection

HeLa cell monolayers ($3\times10^6$) grown in 100 mm plates were infected with wild-type or recombinant polioviruses at a desirable MOI. The viruses were allowed to adsorb to the cells for 1 hr at 37° C. Unbound viruses were removed by washing twice with PBS and 5 ml of pre-warmed DMEM containing 10% FBS was added, after which the cells were incubated in $CO_2$ incubator at 37° C. Following 1 day, a cytopathic effect was examined.

5. Insert Detection and Passage Stability Test by RT-PCR

For proliferation of recombinant polioviruses, HeLa cells were infected at each passage at an MOI of 10 and cultured for 18 hr at 37° C. Total RNA was extracted with phenol-chloroform from the cells and precipitated with ethanol. For cDNA synthesis, 10 µg of the total RNA were mixed with 1 µg of primer and denaturated for 10 min at 70° C. Thereafter, the resultant was transferred to ice and the reverse transcriptase reaction solution (50 mM Tris.HCl, pH 8.3, 65 mM KCl, 3 mM $MgCl_2$, 10 mM DTT, 1 mM NTP mixture, 20 units RNAsin) and 200 units of MMLV (moloney Murine Leukemia virus) reverse transcriptase (Promega) were added, followed by incubation for 60 min at 42° C. After the completion of reaction, the resultant was incubated for 3 min at 100° C. to inactivate enzyme. PCR was then performed using the cDNA prepared as a template and Sabin 1 primers (CATTGAGTGTGTTTACTC: 680–697/sense and GGTAGAACCACCATACGC: 797–814/antisense) to amplify the polioviral genome containing inset sequence. PCR was performed using the model 9700 purchased from Perkin Elmer and Taq polymerase for 25 cycles at 94° C. for 30 sec, 45° C. for 30 sec, and 72° C. for 45 sec. The PCR products were analyzed on agarose gel.

6. Passage Stability Test by Western Blot Analysis

HeLa cells were infected with wild type or recombinant polioviruses at a MOI of 10 at each passage. Cells were harvested 24 hr after infection, washed and resuspended with PBS, and then mixed with the same volume of 2×SDS-PAGE sample buffer (62.5 mM Tris-HCl, pH 6.8, 10% glycerol, 2% SDS, 1% β-mercaptoethanol, 0.03% bromophenol blue, and 0.01 mg/ml Xylene cyanol). After being boiled for 10 min, samples were applied to a SDS-12% polyacrylamide gel electrophoresis (PAGE) and then transblotted to a nitrocellulose membrane using a semi-dry gel transfer system (Bio-Rad). Blotted membranes were screened with mouse anti-poliovirus sera and human anti-poliovirus sera inoculated with OPV and then secondly incubated with alkaline phosphatase (AP)-conjugated goat-anti-mouse (or human)-IgG. The membranes were transferred to a reaction solution containing NBT/BCIP (Sigma) for alkaline phosphatase and the bands with developed color were observed.

7. Single Plaque Isolation

HeLa cells were infected with OPV (oral polio vaccine: Sabin) at $1\times10^2$ $TCID_{50}$ and incubated on a semi solid media containing 1.5% methyl cellulose for 3 days. The plaque purification in which plaques with various morphology and size were isolated was performed under a microscope. For typing plaques, RNAs obtained from plaques purified were amplified by RT-PCR using Sabin type 1-specific primer set [sense(680–697), antisense(814–796); 135 bp], Sabin type 2-specific primer set [sense(681–699), antisense(950–933); 270 bp] and Sabin type 3-specific primer set [sense (723–740), antisense(961–942); 239 bp] to prepare polioviruses as vaccine strains of Sabin types 1, 2 and 3.

8. Animal Test Using Tg-PVR Mouse (1) Optimal Inoculation Conditions of Poliovirus Sabin type 1 to Tg-PVR Mouse The optimal inoculation conditions of poliovirus Sabin type to Tg-PVR mice were established. Firstly, to standardize experimental conditions, the effective inoculation route was determined and then optimal mouse age and inoculation dose and minimal time for post-inoculation immunization were determined. For revealing the optimal inoculation route, intracerebral, intraspinal, intravenous, intramuscular, subcutaneous and intraperitoneal administrations were examined to induce the formation of antibodies. A microsyringe and specially designed 26/30 gauge needles were used for minimizing the damage associated with intracerebral and intraspinal inoculation. For intravenous, subcutaneous and intraperitoneal inoculation, 26 gauge needle was used. A sonde for mouse was used for oral administration.

(2) Immunization with RPS/r-OPV

Tg-PVR mice infected with wild type poliovirus is very likely to exhibit the development of paralysis similar to human case and show significant lethality. In addition, it has been reported that they show higher specificity to each serotype of polioviruses (Koike, S. C. et al., *PNAS. USA*, 88:951–955(1991)). Therefore, the present inventors have contemplated that the Tg-PVR mice could provide a reliable prevention animal model. It was examined whether RPS/r-OPV (recombinant-oral polio vaccine) of this invention could induce immunization to either types 2 and 3 or all types of poliovirus.

9. In Vitro Neutralization Assay

Antisera (antibodies) against vaccine gene-encoding proteins prepared by intracerebral or intramuscular inoculation to Tg-PVR mouse, and wild type polioviruses (Mahoney, W-2, Lansing and Leno) or Sabin types 1, 2 and 3 polioviruses were mixed for evaluating a neutralization potency. In vitro neutralization assay was performed with 96-well culture plate according to a standard microtiter assay. The antibody to each serotype and control antiserum (normal serum from Tg-PVR mouse and placebo) were diluted and mixed with serially diluted virus to incubate for 2 hr at 37° C. To verify that viruses were neutralized with neutralizing Abs, HeLa cells ($1 \times 10^3$) were added to each well and incubated for 3 days, followed by staining with 1% crystal violet to evaluate the occurrence of cytopathic effect. Simultaneously, the titration of each virus was performed to reveal a neutralized virus titer.

10. Protection and Prevention Test by Poliovirus Infection

Tg-PVR mice were classified 3 groups. Group 1 as a positive control group was immunized by infecting Tg-PVR mouse with Sabin type 1, 2 or 3 poliovirus as a vaccine strain. Group 2 was immunized by inoculating Tg-PVR mouse with MucOra-Vax/rec-OPV of this invention via intramuscular route. Group 3 was immunized with inactivated poliovirus. The wild type polioviruses, Mahoney, Lansing and Leon were infected at $1 \times 10^7$ $TCID_{50}$ to verify the prevention efficacy.

Results

1. Analysis of Specificity to Serotype Using Antiserum 1.1 Western Blot Analysis of Poliovirus Antigen using Poliovirus Antiserum Using antiserum from Tg-PVR mouse inoculated with wild type 2 and 3 polioviruses, Western blotting was carried out against conjugated epitope peptide of each serotype and virus-infected HeLa cell lysate. As a result, viral protein containing the whole VP1 region was detected in serotype-specific manner. However, the neutralizing epitope peptide inserted was not detected, so that it could be realized that the antiserum contains no Abs to recognize a linear form of the epitope. It could be appreciated that the neutralizing epitope expressed in recombinant RPS-Vax vector was rarely detected by Western blot analysis using virus antiserum because the neutralizing epitope introduced by this invention was a conformational epitope (see FIG. 3).

1.2 Western Blot Analysis using Epitope Peptide-Induced Antiserum

The VP1 neutralizing epitopes of the wild type 2 and 3 polioviruses were synthesized in a conjugated form with BSA and BALB/c mice were immunized with them to prepare polyclonal Ab (hereinafter referred to as pAb). It was evaluated in a Western blot analysis whether the pAbs could recognize VP1 protein of each serotype. As a result, it was revealed that the epitope-derived antiserum could well recognize VP1 of each serotype of wild-type polioviruses and its vaccine strain (see FIG. 4).

Figure 4:
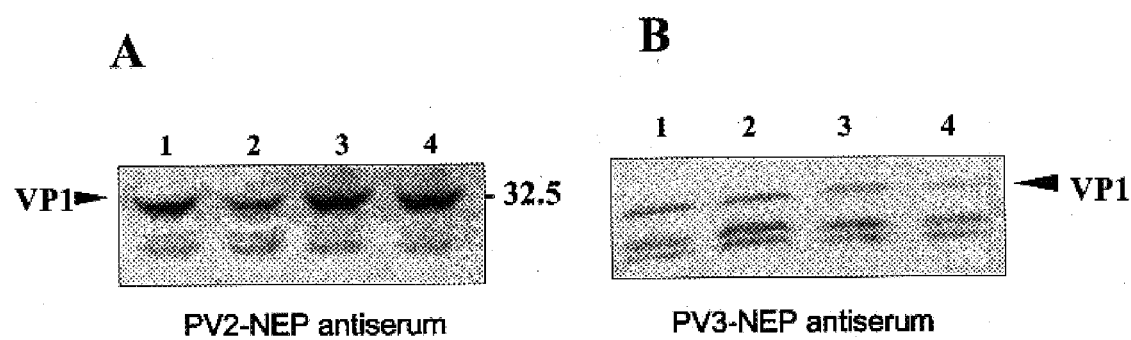
FIG. 4 represents the results of Western blot analysis using polyclonal antibody induced with PV2-NEP-BSA conjugate or PV3-NEP-BSA conjugate. In panel A, lanes 1, 2, 3, 4 and M represent Sabin type 2, W-2 (VR-301, ATCC), Lansing (VR-1002, ATCC), Lansing (VR-1002, subcultured) and marker, respectively. In panel B, lanes 1, 2, 3, 4 and M represent Sabin type 3, Leon (VR-1004, ATCC), Leon (VR-62, ATCC), Leon (VR-62, subcultured) and marker, respectively.

The pAb obtained using PV2-NEP peptide was revealed to considerably recognize VP1 of Sabin type 2 virus, W-2 strain (wile type 2), Lansing strain and subculture of Lancing strain (see panel A of FIG. 4). The pAb prepared using PV3-NEP peptide was revealed to remarkably recognize VP1 of Sabin type 3 virus, type 3 Leon strain (VR-1004), Leon strain (VR-62) and subculture of Leon strain (VR-62) (see panel B of FIG. 4).

Based on the results of these experiments, it would be appreciated that pAbs prepared using epitope peptides are suitable in experiments to examine expression of recombinant antigens in recombinant Sabin type 1 vectors of this invention and stability (protein folding) of recombinant antigen expressed.

1.3 Recognition of Neutralizing Antibody to Conformational Epitope

Experiments were carried out in order to verify that antisera obtained by immunizing with either viruses or epitopes may recognize neutralizing epitope of each serotype of polioviruses to neutralize virus. In vitro neutralization assay was performed on 96-well culture plates according to a standard microtiter assay.

Figure 5:
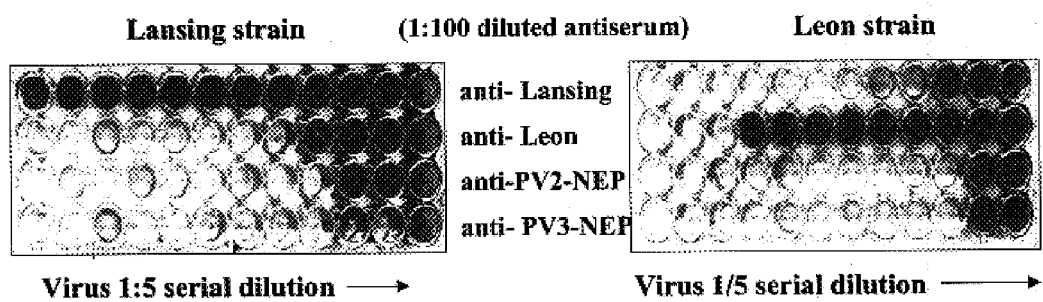
FIG. 5 represents the results of in vitro neutralizing assay using neutralizing antibodies in antisera obtained from the mice immunized with poliovirus type 2 or 3 or neutralizing epitope of poliovirus type 2 or 3.

Ab of each serotype and control antiserum (normal serum from Tg-PVR mouse) were diluted to 1:100 and mixed with serially diluted Lansing or Leon viruse (1:5), followed by incubating for 2 hr at 37° C. To investigate that viruses were neutralized with neutralizing Abs contained antisera, HeLa cells ($1 \times 10^3$) were added to each well and incubated for 3 days and stained with 1% crystal violet to evaluate the occurrence of cell lysis. Simultaneously, the activity of neutralizing Ab of each serotype was examined. The results show that only anti-virus serum exhibits potential serotype-specific neutralizing activity but antiserum prepared using peptide exhibits no neutralizing activity (see FIG. 5). Therefore, it could be realized that the poliovirus neutralizing antibody could recognize the conformation of a specific amino acid sequence but not linear epitope. The results are summarized in Table I.

TABLE I

| | Result of Western blot Antigen | | |
|---|---|---|---|
| Serum sample | Viral VP1 | Epitope peptide | Neutralization of poliovirus |
| Serum from virus-infected Tg-PVR mouse | + | − | + |
| Serum from Peptide-immunized BALB/c mouse | + | + | − |

2. Evaluation of Antibody Specificity between Serotype

The purpose of RPS-Vax/OPV development is to develop oral polio vaccine with safety capable of neutralizing all of 3 serotypes. The RPS-Vax/OPV may be constructed by integrating into the RPS-Vax system neutralizing epitopes of Sabin type 2 and 3 responsible for VAPP. In addition, the purpose of this invention is to suggest Tg-PVR transgenic mouse as a preclinical animal model for testing a prevention efficacy of polio vaccines. To exactly test the prevention efficacy, it is necessary that the immunity induced by Sabin type 1 as a backbone of RPS-Vax vector do no exhibit cross-neutralizing immunity toward Sabin type 2 and 3.

2.1 Cross Immunity Test by Western Blot

To verify the induction of cross immunity between serotype, Sabin type 1, 2 and 3 viruses were intracerebrally inoculated into Tg-PVR mouse and antiserum was isolated for Western blot (FIG. 6a). Western blot was performed with respect to all serotypes. The results show that the antiserum against each of Sabin type 1, 2 and 3 could well recognize its respective VP1. In addition, it was observed that the cross immunity between serotype does not occur.

In the meantime, the wild type polioviruses, Mahoney, Lansing and Leon strains were inoculated into Tg-PVR mouse and antiserum was isolated to verify the induction of cross immunity between serotype. Western blot was carried out (FIG. 6b). As represented in FIG. 6b, antiserum of human inoculated with oral polio vaccine significantly recognizes VP1 of all of wild type polioviruses. In contrast to this, mouse antiserum to each serotype specifically recognizes VP1 of each serotype virus, showing no cross immunity.

2.2 Cross-Neutralizing Activity Test

To confirm whether the serotype-specific immunity revealed by Western blot is also practically effective in neutralization of virus, in vitro neutralization assay was carried out. The antiserum used in the Western blot analysis was diluted to 1:100 and tested to examine the occurrence of cross-neutralizing due to cross immunity with respect to Mahoney, Lansing and Leno strains. As summarized in Table II, the antiserum to Sabin type 1 contains no cross-neutralizing antibodies to neutralize type 2 and 3 viruses.

Accordingly, it would be anticipated that the recombinant vaccine of RPS-Vax vector, the improved OPV of this invention may be exactly examined without unspecific immune reaction in a preclinical animal test using Tg-PVR mouse in view of protection immunity efficacy.

TABLE 2

| Target Poliovirus | Antiserum | | | |
|---|---|---|---|---|
| | Media | Sabin-1 | Sabin-2 | Sabin-3 |
| Mahoney | 0 | 2900 | 3 | 3 |
| Lansing | 0 | 9 | 2750 | 9 |
| Leon | 0 | 3 | 0 | 3120 |

3. Design and Expression of Conformational Epitope 3.1 Epitope Mapping and Design of Poliovirus Type 2 and 3

According to previous studies, poliovirus has a pocket structure called as canyon in virus attachment site, a binding site to the poliovirus receptor of host cells, and therefore neutralizing antibodies are urged to block the binding site for neutralization. Neutralizing epitopes of poliovirus serotype have been well elucidated. However, our intensive experiments have revealed that antiserum obtained from animals expressing the whole neutralizing epitope sequence showed little or no neutralizing potency. These results demonstrate that a neutralizing epitope of poliovirus is able to induce the generation of neutralizing antibodies only when it has a specific and correct conformation.

In this connection, the present inventors have designed conformational epitopes to induce the generation of neutralizing antibodies by molecular modeling and hydropathy scanning. Firstly, we selected candidate sequences of a conformational epitope based on NMR data with crystals of the binding form between poliovirus and its receptor (PVR: human poliovirus receptor) and hydropathy plot of amino acid sequence. Such candidate sequences containing neutralizing epitope sequence were predictive of being folded in a domain and maintaining native epitope conformation.

Figure 7A:
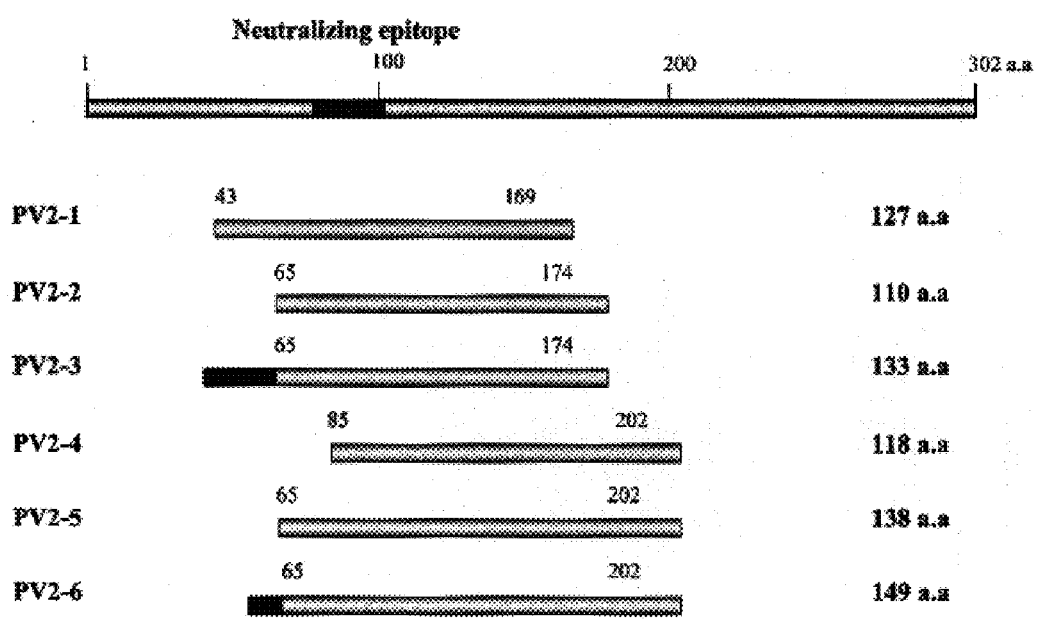
FIGS. 7*a* and 7*b* represent conformational epitope regions from poliovirus type 2 and 3, respectively.
Figure 7B:
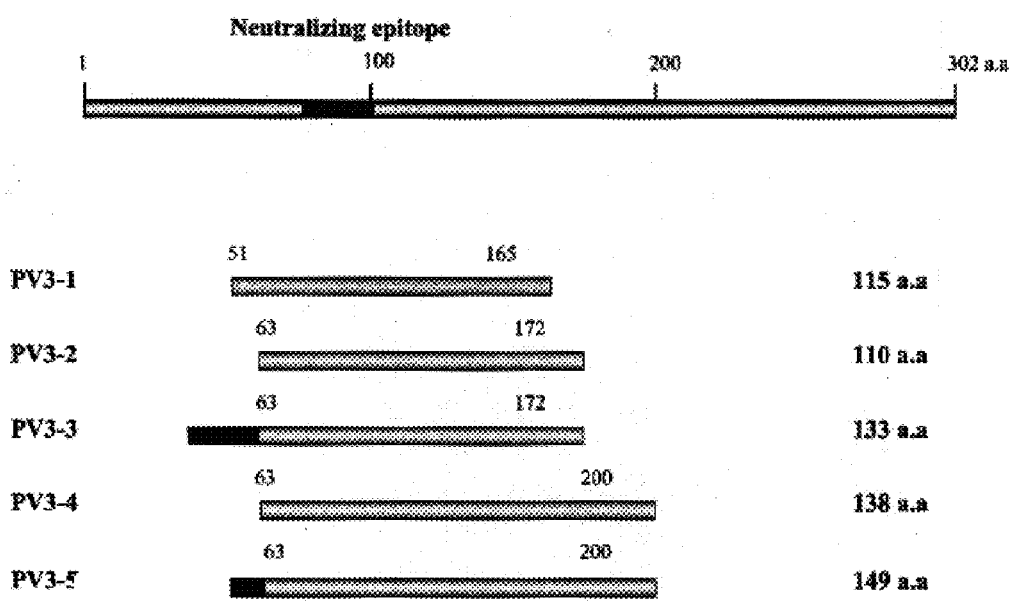
Figure 8A:
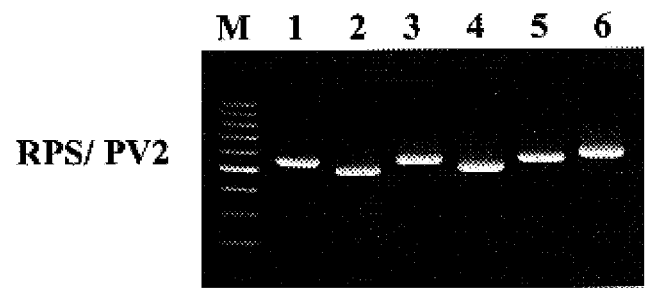
FIG. 8*a* is the RT-PCR of the insert sequence, originated from type 2 or 3 poliovirus and integrated into RPS-Vax-derived recombinant poliovirus.
Figure 8A:
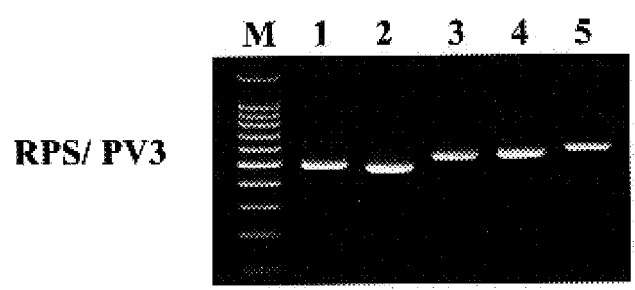
Figure 8B:
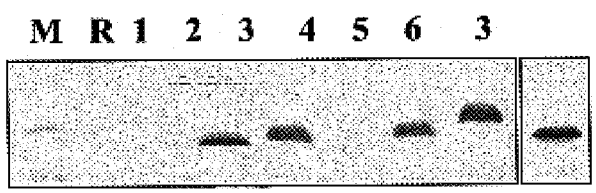
FIG. 8*b* is the Western blot of the insert proteins expressed from the recombinant poliovirus.
Figure 8B:
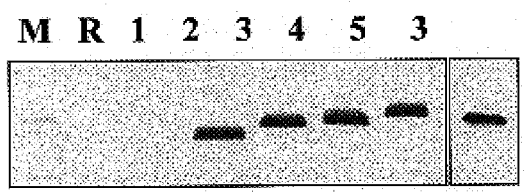

FIGS. 7a and 7b represent some of candidate sequences selected. In FIGS. 7a and 7b, a shorter shade sequence represents PTD (protein transduction peptide) derived from HIV-1 Tat protein and a longer shade sequence corresponds to Tag sequence. The amino acid sequences of PTD and Tag used are YGRKKRRQRRR and SMTGG QQMGR DLYDD DDKDR WGS, respectively.

3.2 Expression and Genetic Stability of Antigen Gene (Insert Sequence)

Poliovirus type 2:W-2 (or Lansing) or type 3:Leon strains was introduced into the HeLa cells and incubated for 18 hr at 37° C. In each passage, HeLa cell monolayers were infected with the virus at an MOI of 10, and then the polioviruses were harvested, followed by phenol-chloroform extraction and ethanol precipitation to obtain total RNA. Then, 10 μg of RNA were mixed with 1 μg of primer (5'-TTT TTT TTT TTT TTT TTT-3') and denatured for 10 min at 70° C. Thereafter, the resultant was transferred to ice and the reverse transcriptase reaction solution (50 mM Tris.HCl, pH 8.3, 65 mM KCl, 3 mM MgCl$_2$, 10 mM DTT, 1 mM NTP mixture, 20 units RNAsin) and 200 units of MMLV (moloney Murine Leukemia virus) reverse transcriptase (Promega) were added, followed by incubation for 60 min at 42° C. to prepare cDNA.

Thereafter, based on the information obtained from epitope mapping, the antigen genes of type 2 and type 3 polioviruses and the combined antigen gene of type 2 and type 3 were determined and amplified by PCR using a primer set containing cloning enzyme sites (SstII and EagI). PCR was performed with the machine 9700 purchased from Perkin Elmer and PWO DNA polymerase (Boehringer Mannheim, Cat#: 1644947) for 25 cycles at 94° C. for 30 sec (denaturation), 47° C. for 30 sec (annealing) and 72° C. for 1 min (extension). The sequences of primers used are as follows:

PV2-138/s (ATT ATT CCgCgg CAC gTC ATC CAA AAg Cg),

PV2-138/a (AAT ATA CggCCg AAT gCC CAC gTA ggg CA),

PV3-138/s (ATT ATA CCgCGg CAC gTA gTC CAA CgA Cg), and

PV3-138/a (ATA TTA CggCCg ggC TAA CCC CAC gTA Tg).

Figure 9:
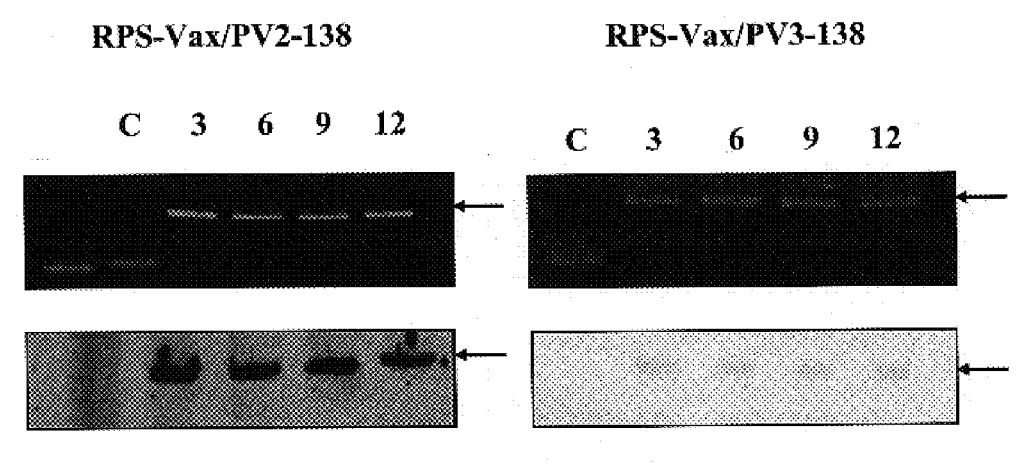

Each PCR product was inserted between SstII (NEB, Cat#:157S) and EagI (NEB, Cat#:505S) restriction sites in the multiple cloning site of RPS-Vax and amplified in *E. coli* JM109 host cells (STRATAGENE, Cat#:200235) to produce RPS/r-OPV candidates. The expression pattern of the vaccine candidates was examined (see FIG. 8). As shown in FIG. 9, the vaccine candidates, recombinant RPS-Vax/PV2-138 and RPS-Vax/PV3-138 polioviruses exhibit improved genetic stability in serial passages.

4. Evaluation of Efficacy Test Using Tg-PVR Mouse 4.1 Proliferation of Poliovirus in Tg-PVR Mouse Tg-PVR mouse inoculated with 5×10$^6$ TCID$_{50}$ Sabin type 1 without foreign antigen gene was revealed to largely generate antibodies against VP1 from 2 weeks after inoculation. Such pattern of antibody production was sustained more than 12 weeks. Furthermore, the same amount of Sabin type 1 treated with ultraviolet ray for 15 min to extinguish its infectivity was injected into Tg-PVR mouse under the same conditions as normal virus, resulting in no formation of antibodies to poliovirus (see FIG. 10c). These results could lead us to reason that Sabin type 1 poliovirus effectively infects into Tg-PVR mouse and only its live form induces the generation of antibody. In addition, these results demonstrate that lower titer of Sabin type 1 virus is sufficient to induce immunization in Tg-PVR mouse. Although Sabin type 1 proliferated to some extent in ICR mouse, the titer of antibody to VP1 in PVR transgenic mouse was shown to be much higher than ICR mouse, demonstrating PVR effect.

4.2 Optimal Inoculation Route and Dose

Each group consisting of 3 Tg-PVR mice was infected with the same dose of RPS-Vax by intracerebral, intravenous, intramuscular, subcutaneous, intraperitoneal, oral or mucosal administration. After 6 weeks of administration, antisera from mouse of each group were collected and analyzed by the Western blot to reveal the titer of antibody formed. As shown in panel A of FIG. 10, mice inoculated via intracerebral, intravenous, intramuscular or intraperitoneal route were revealed to show higher titer of antibody to VP1. Furthermore, the Western blot analysis after 12 weeks of administration also showed the similar results. With comparing the Western blot results of 6 week- and 12 week-administration, it was elucidated that only intracerebral and intramuscular injections enabled the titer of antibody to maintain to 12 weeks.

For determining the optimal inoculation dose, Sabin type 1 polioviruses were intramuscularly injected with increasing its dosage from $2 \times 10^3$ to $2 \times 10^7$ $TCID_{50}$ and then the Western blot analysis was carried out. The most preferable inoculation dose was determined $1 \times 10^7$ $TCID_{50}$ (see panel B of FIG. 10).

Based on the results described previously, it was determined that the immunization of Tg-PVR mouse would be performed by intramuscular injection for inoculation facility and minimization of error.

Figure 10:
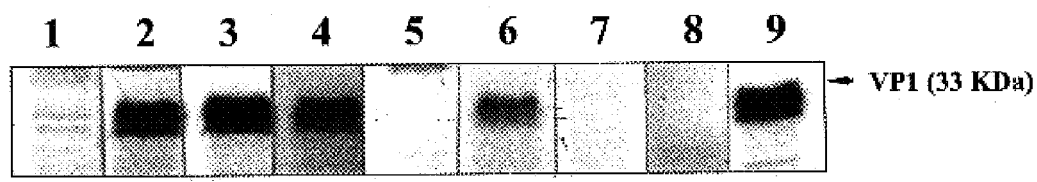
FIG. 10 represents effects of doses and inoculation routes on the immunogenicity of the virus in Tg-PVR mice, which were analyzed by Western blot. Panel A represents the efficacies of different inoculation routes in Tg-PVR mouse. Panel B represents efficacies of different doses of Sabin type 1 in Tg-PVR mouse. Panel C shows the Western blot analysis of antiserum obtained from the Tg-PVR mouse inoculated with live or UV-inactivated Sabin type 1. Lane "Media/Tg-PVR" represents medium-inoculated control antiserum, lane "Sabin 1 (UV)/Tg-PVR" represents antiserum obtained from the Tg-PVR mice inoculated with the recombinant virus ($1 \times 10^7$ pfu) inactivated by ultraviolet (UV) ray and lane "RPS-Vax/Tg-PVR" represents antiserum obtained from the Tg-PVR mice inoculated with live recombinant virus ($1 \times 10^7$ pfu).
Figure 10:
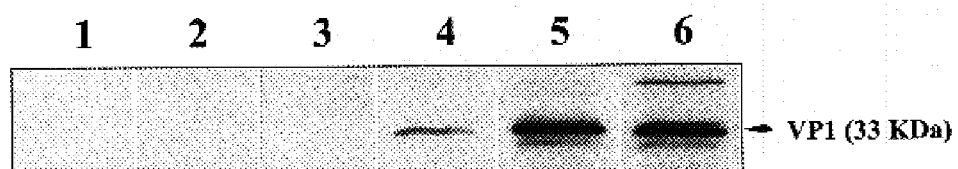
Figure 10:
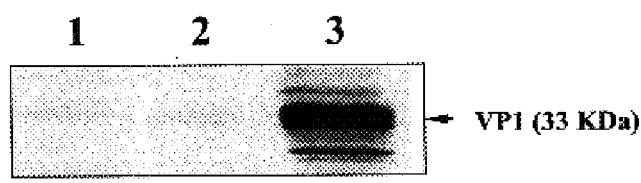

The results in which the same amount of Sabin type 1 treated with ultraviolet ray for inactivation resulted in no formation of antibodies to VP1, urged us to reason that VP1-specific antibodies are induced through virus proliferation (see panel C of FIG. 10).

5. Animal Prevention Model for Improved OPV 5.1 Control Vaccine Test

Tg-PVR mice were inoculated with polioviruses of Sabin type 1, 2 and 3 as a control vaccine showing no cross immunity and in vitro neutralizing assay was performed to examine the formation of neutralizing antibodies. In addition, the mouse groups inoculated with 3 serotypes of Sabin were infected with each wild type of poliovirus and the occurrence of poliomyelitis was evaluated to determine the prevention efficacy. For challenging experiment, the optimal dose of the wile type poliovirus for challenging was determined $1 \times 10^7$ $TCID_{50}$ (5–10 fold higher than $LD_{50}$) and the optimal inoculation route was determined intramuscular injection. The results are summarized in Table III.

TABLE III

| Vaccine | Challenge | Incidence of poliomyelitis or death (%) | Prevention results |
|---|---|---|---|
| Sabin-1 | Mahoney | 0 | 8/8 |
| Sabin-1 | Lansing | 100 | 0/11 |
| Sabin-1 | Leon | 100 | 0/8 |
| Sabin-2 | Mahoney | 100 | 0/7 |
| Sabin-2 | Lansing | 6.7 | 14/15 |
| Sabin-2 | Leon | 100 | 0/8 |
| Sabin-3 | Mahoney | 100 | 0/6 |
| Sabin-3 | Lansing | 100 | 0/6 |
| Sabin-3 | Leon | 8.3 | 11/12 |

5.2 Analysis of Neutralizing Antibody Generation and Prevention Efficacy

As the results of in vitro neutralizing assay, it was observed that RPS/PV2-138 and RPS-PTD/PV2-138 in type 2 poliovirus and RPS/PV3-138 in type 3 poliovirus induced the highest titer of neutralizing antibody (see FIG. 11). As shown in panel B of FIG. 11, RPS-Vax/PV2-110-Tag could not induce neutralizing antibody even when inactivated Sabin type 2 was secondly inoculated, leading us to suggest that neutralizing antibody is not induced by only the secondary inoculation of inactivated Sabin type 2. In contrast, mice being subjected to the first inoculation with RPS/PV2-138 and RPS-PTD/PV2-138 and the secondary inoculation with inactivated Sabin type 2 produced neutralizing antibodies with the level of 60% compared to control group being subjected to the thrice inoculations of Sabin type 2 live vaccine. Similarly, when mice were inoculated with RPS-Vax/PV3-138 recombinant vaccine strain and further inoculated twice with inactivated Sabin type 3, they generated neutralizing antibodies with the level of 80% compared to control group being subjected to the thrice inoculations of Sabin type 3 live vaccine. However, mice being subjected to the first inoculation with RPS-Vax or RPS-Vax/PV3-100-Tag recombinant viruse and the second inoculation with inactivated Sabin type 3 produced little or no neutralizing antibody against Leon strain. On the basis of these results, it would be suggested that RPS-Vax/PV2-138 (RPS-Vax/PV3-138) could elicit the formation of B cell clones to type 2 (3) poliovirus and B cell clones are amplified by boost inoculation with inactivated Sabin type 2 (3), resulting in the efficient production of neutralizing antibodies to type 2 (3) poliovirus. The control group being subjected to twice inoculations with inactivated Sabin type 2 (3) produced no neutralizing antibody, suggesting that neutralizing antibodies generated are not induced by inactivated Sabin type 2 and 3.

Furthermore, Tg-PVR mice infected with each recombinant poliovirus were inoculated with various concentrations of each poliovirus (Mahoney, Lansing and Leon) to test prevention immunity potential of chimeric viruses. After inoculation, mouse groups showing prevention effect at 10 $LD_{50}$ were examined and in vivo survival of viruses was evaluated. Combining theses results with the results of in vitro experiments, we selected a recombinant polio live vaccine candidate (RPS-Vax/r-OPV; abbreviated as r-OPV) with mixing RPS/PV2-138 and RPS/PV3-138 chimeric viruses exhibiting excellent prevention efficacy. The genetic stability, induction of neutralizing antibody and prevention potency of the vaccine candidates are summarized in Table IV.

TABLE IV

| r-OPV | Genetic stability (passage no.) | Western blot | Neutralizing antibody (after 3rd I.N) | Survival rate (challenge) |
|---|---|---|---|---|
| *Lansing* | | | | |
| RPS/PV2-127 | >12 | − | N.A | 0/3 |
| RPS/PV2-110 | >12 | + | − | 0/6 |
| RPS-Tag/PV2-110 | >12 | + | − | 0/6 |
| RPS/PV2-118 | >12 | − | N.A | 0/6 |
| RPS/PV2-138 | >12 | + | +++ | 9/9 |
| RPS-PTD/PV2-138 | >12 | + | +++ | 9/9 |
| *Leon* | | | | |
| RPS/PV3-115 | >12 | − | N.A | 0/3 |
| RPS/PV3-110 | >12 | + | − | 0/6 |
| RPS-Tag/PV3-110 | >12 | + | + | 2/9 |
| RPS/PV3-138 | >12 | + | +++ | 9/9 |
| RPS-PTD/PV3-138 | <4 | + | − | 0/9 |

5.3 Development of r-OPV Vaccine Program 5.3-1: Evaluation of Formation of Neutralizing Antibody The improved polio vaccine candidates (RPS/PV2-138 and RPS/PV3-138: r-OPV) were mixed at an equal inoculation dose ($1 \times 10^7$ TCID$_{50}$) and intramuscularly inoculated into Tg-PVR mice. After 4 weeks, commercially available IPV (inactivated polio vaccine; Avantes Korea, Inc. 0.5 ml/vial) was additionally inoculated twice with various doses at 2-week interval. After 10 days of the final inoculation, the blood samples were collected from mice and subject to in vitro neutralizing assay to reveal the formation of neutralizing antibody against each wild type of poliovirus (Mahoney, Lansing and Leon). In addition to this, the same assay as described above was carried out for conventional OPV-OPV-OPV, IPV-IPV-IPV and IPV-OPV-OPV programs.

Figure 12A:
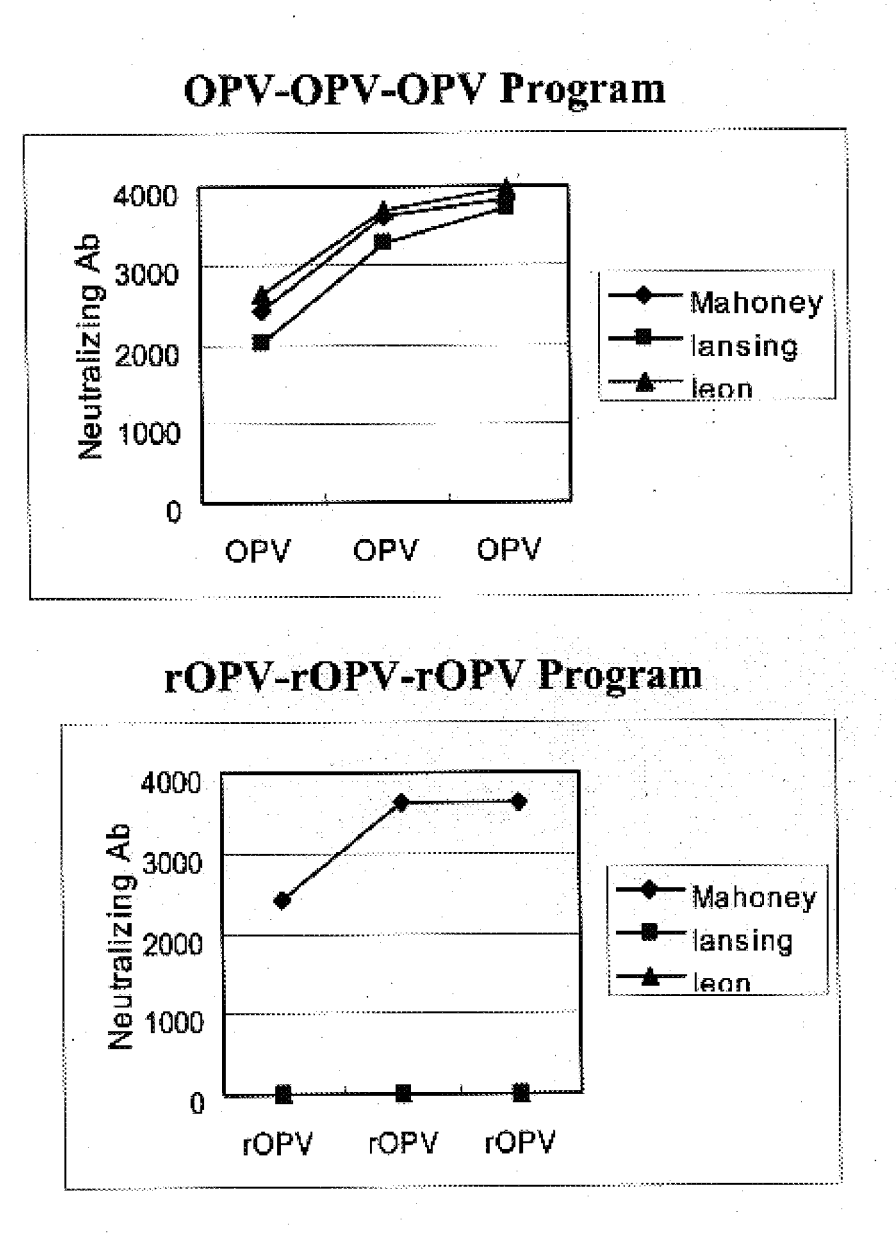
Figure 12B:
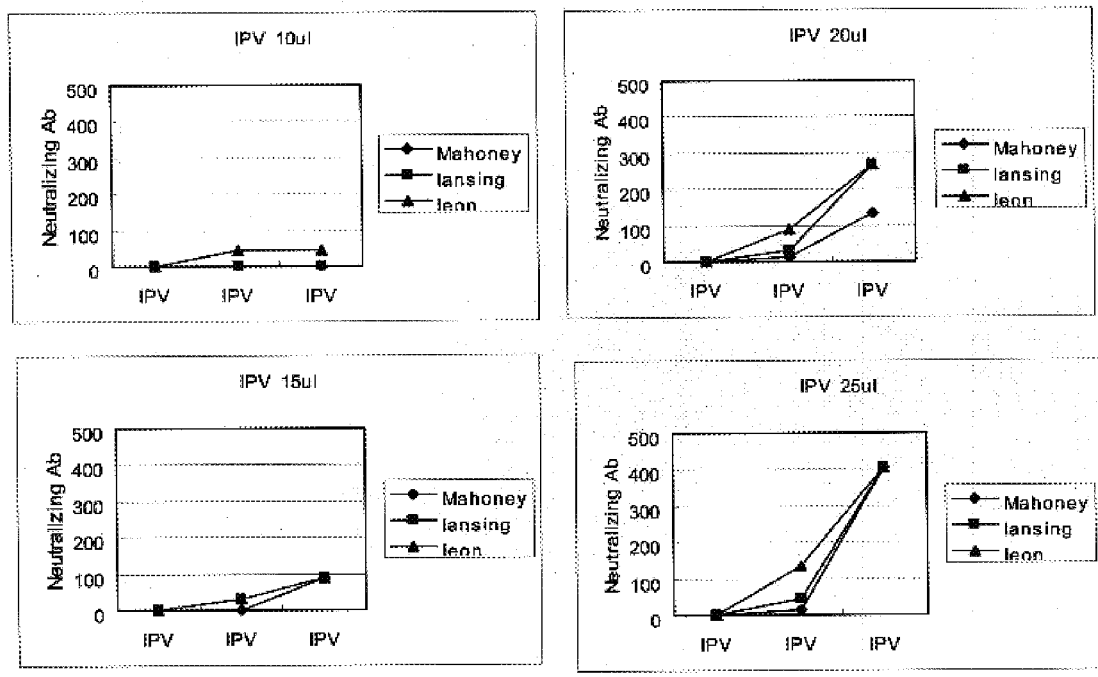
Figure 12C:
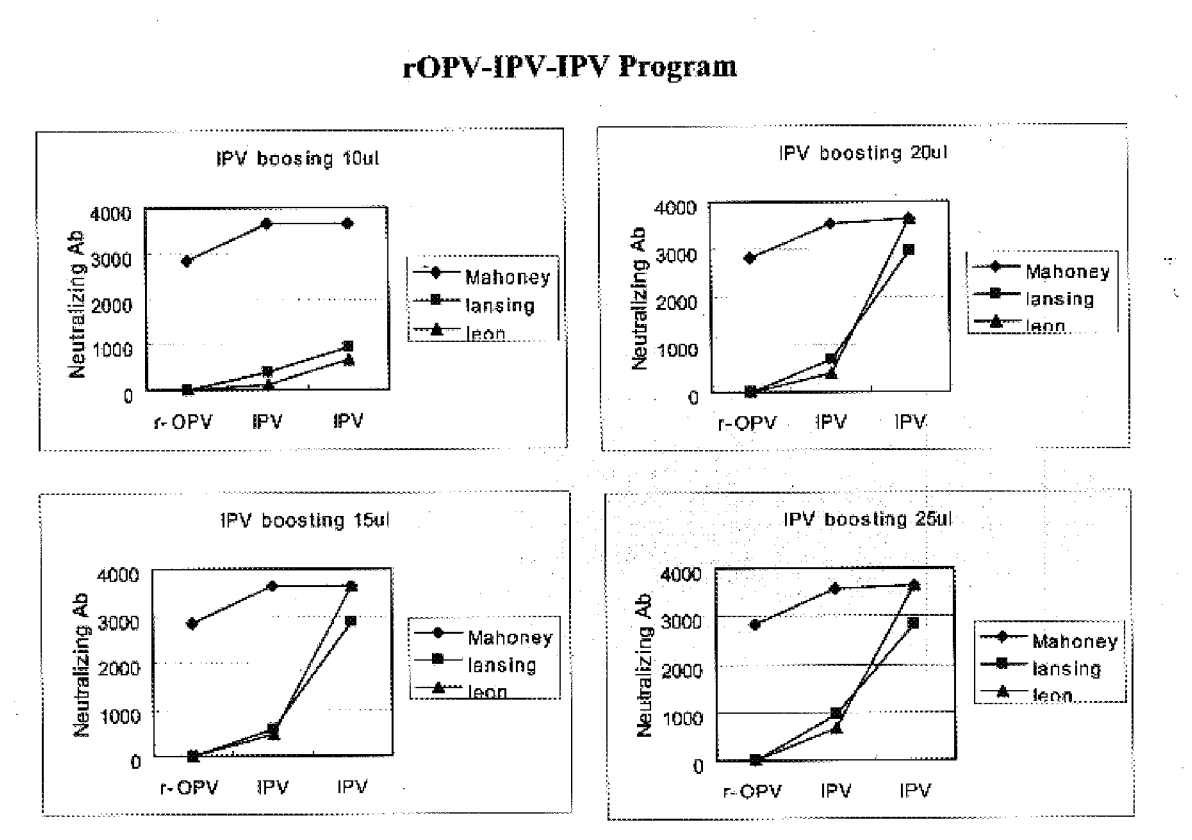

As a result, the conventional OPV-OPV-OPV program induced the highest titer of neutralizing antibody as expected (see panel A of FIG. 12a). When r-OPV was inoculated three times, neutralizing antibodies to type 2 and 3 polioviruses were not induced (see panel B of FIG. 12a). However, where more than 15 μl of IPV were additionally inoculated twice after the inoculation of r-OPV, the neutralizing antibody to Leon strain was induced with the level of 87% compared to the positive control (OPV-OPV-OPV program) and the neutralizing antibody to Lansing strain was induced with the level of 75% compared to the positive control (see FIG. 12c). The IPV-IPV-IPV program with 15 μl inoculation volume induced neutralizing antibody with the level of less than 1/30 of the positive control (OPV-OPV-OPV program) and that with 25 μl inoculation volume induced neutralizing antibody with the level of less than 1/10 of the positive control (see FIG. 12b).

Based on these results, it would be recognized that r-OPV program of this invention (r-OPV-IPV-IPV) could induce neutralizing antibody much more effectively than IPV-IPV-IPV and IPV-OPV-OPV programs (alternative program promoted in USA) even when much less dose of IPV than the conventional IPV-IPV-IPV program is used.

According to our experiments, the IPV-OPV-OPV program showed the declined effect of boosting inoculations with OPV when the inoculation dose of IPV increases. In addition, it was elucidated that where the inoculation dose of IPV decreases, the boosting inoculations with OPV induced higher titer of neutralizing antibody. However, such increasing pattern is ascribed to immunity induction by OPV rather than amplification of B cell clone induced by IPV; therefore, there remains the problem of VAPP risk associated with OPV. Our repetitive experiments showed that the titer of neutralizing antibody from mice immunized by r-OPV vaccine program of this invention reaches to at least 80% compared to OPV-OPV-OPV program.

5.3-2: Prevention Efficacy

The improved polio vaccine candidates (r-OPV: RPS/PV2-138 plus RPS/PV3-138) were mixed at an equal inoculation dose ($1 \times 10^7$ TCID$_{50}$) and intramuscularly inoculated into Tg-PVR mice. After 4 weeks, sIPV (Sabin-derived IPV) prepared by inactivating Sabin type 1, 2 and 3 viruses with formalin was additionally inoculated twice at 2-week interval, followed by challenging with $1 \times 10^7$ TCID$_{50}$ of each wild type poliovirus to evaluate prevention efficacy. In addition, the same experiments as described above were carried out in accordance with the conventional OPV-OPV-OPV, sIPV-sIPV-sIPV and sIPV-OPV-OPV programs. For further comparison, the VP1 neutralizing epitope substitution vaccine, Sain-1/Leon, was constructed and analyzed.

As a result, the r-OPV-sIPV-sIPV program of this invention was elucidated to exhibit the prevention potency around 100% as the OPV program. Although the sIPV-OPV-OPV program currently promoted as an alternative program in USA showed significant prevention potency, this program did not induce sufficient titer of neutralizing antibody (15% of OPV-OPV-OPV program) and gave rise to death of mouse with paralysis (1/5). In addition, it was revealed that the substitution vaccine, Sain-1/Leon, partially showed prevention efficacy and sIPV-sIPV-sIPV showed no prevention efficacy resulting in death of all experimental mice within 1 week. The results are found in Table V.

TABLE V

| Vaccination | | | Prevention | | | Titer of neutralizing Ab* (%)** |
|---|---|---|---|---|---|---|
| 1st | 2nd | 3rd | Mahoney | Lansing | Leon | |
| Sabin-1, 2 and 3 (OPV) | Sabin-1, 2 and 3 (OPV) | Sabin-1, 2 and 3 (OPV) | 12/12 | 12/12 | 12/12 | 100 |
| Sabin-1, 2 and 3 (sIPV***) | Sabin-1, 2 and 3 (OPV) | Sabin-1, 2 and 3 (OPV) | 6/6 | 5/6 | 6/6 | 15 |
| Sabin-1, 2 and 3 (sIPV) | Sabin-1, 2 and 3 (sIPV) | Sabin-1, 2 and 3 (sIPV) | 0/3 | 0/3 | 0/3 | 0 |
| RPS-Vax (Sabin-1) | Sabin-1, 2 and 3 (sIPV) | Sabin-1, 2 and 3 (sIPV) | 6/6 | 0/6 | 0/6 | 0 |
| r-OPV | Sabin-2 and 3 (sIPV) | Sabin-2 and 3 (sIPV) | 6/6 | 6/6 | 6/6 | >80 |

TABLE V-continued

| Vaccination | | | Prevention | | | Titer of neutralizing |
| --- | --- | --- | --- | --- | --- | --- |
| 1st | 2nd | 3rd | Mahoney | Lansing | Leon | Ab* (%)** |
| Sabin-1/Leon (chimera) | Sabin-1/Leon (chimera) | Sabin-1/Leon (chimera) | 3/3 | 0/3 | 2/6 | 30 (Leon) |

*measured simultaneously using all 3 serotypes
**calculated with referring to Ab titer of OPV-OPV-OPV as 100%
***prepared by inactivating Sabin strains with formalin Currently, the advanced countries intend to avoid following the OPV-OPV-OPV program because it elicits VAPP. Furthermore, in the case of the IPV-OPV-OPV program accompanied with high cost, the efficacy of live vaccine is very likely to decrease owing to neutralization induced by IPV and the risk of VAPP occurrence still remains due to use of live Sabin-2 and Sabin-3. In contrast, since the r-OPV program of this invention adopts neutralizing epitopes of type 2 and 3 polioviruses and employs no live Sabin type 2 and 3, it exhibits prominent safety and prevention efficacy.

In the meantime, the IPV-OPV-IPV program used in Western countries shows low efficacy and requires a large amount of the wild type poliovirus for production of vaccines (10 L culture for vaccination of 15 persons). However, since the r-OPV-IPV-IPV program of this invention could induce satisfactory immunization similar to the OPV program even with much lower dose as demonstrated previously, the production cost for vaccine can be considerably reduced.

In summary, the r-OPV-IPV-IPV program of the instant invention can overcome the shortcomings of conventional polio vaccine programs and therefore may be highlighted as a novel polio vaccine program.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A recombinant Sabin type 1 poliovirus vector, which comprises:
   (a) a genomic nucleotide sequence of a Sabin type 1 poliovirus;
   (b) a nucleotide sequence encoding an additional polioviral cleavage site; and
   (c) a nucleotide sequence of less than 450 base pairs encoding a conformational epitope wherein said conformational epitope is selected from the group consisting of: a VP1 neutralizing epitope of poliovirus type 2 which is the sequence of amino acids 65–202 of SEQ ID NO:1, and a VP1 neutralizing epitope of poliovirus type 3 which is the sequence of amino acids 63–200 of SEQ ID NO:2.

2. The recombinant Sabin type 1 poliovirus vector according to claim 1, wherein said additional polioviral cleavage site is a cleavage site for poliovirus 3C protease or poliovirus 2A protease.

3. The recombinant Sabin type 1 poliovirus vector according to claim 2, wherein said additional polioviral cleavage site is a cleavage site for poliovirus 3C protease.

4. The recombinant Sabin type 1 poliovirus vector according to claim 1, wherein said nucleotide sequence encoding the conformational epitope comprising the VP1 neutralizing epitope of poliovirus type 2 comprises the nucleotide sequence of SEQ ID NO: 7.

5. The recombinant Sabin type 1 poliovirus vector according to claim 1, wherein said nucleotide sequence encoding the conformational epitope comprising the VP1 neutralizing epitope of poliovirus type 3 comprises the nucleotide sequence of SEQ ID NO: 8.

6. A vaccine composition comprising (a) the recombinant Sabin type 1 poliovirus vector of any one of claims 1–4 and 5 and (b) a pharmaceutically acceptable carrier.

7. The vaccine composition according to claim 6, wherein said recombinant Sabin type 1 poliovirus is a combination of (i) a recombinant Sabin type 1 poliovirus comprising the nucleotide sequence encoding the conformational epitope comprising the VP1 neutralizing epitope of poliovirus type 2;
   and (ii) a recombinant Sabin type 1 poliovirus comprising the nucleotide sequence encoding the conformational epitope comprising the VP1 neutralizing epitope of poliovirus type 3.

8. A method for immunizing an individual against poliovirus, which comprises administering to the individual a vaccine composition comprising (i) the recombinant Sabin type 1 poliovirus vector of claim 1 and (ii) a pharmaceutically acceptable carrier.

9. The method for immunizing according to claim 8, wherein said additional polioviral cleavage site is a cleavage site for poliovirus 3C protease or poliovirus 2A protease.

10. The method for immunizing according to claim 9, wherein said additional polioviral cleavage site is a cleavage site for poliovirus 3C protease.

11. The method for immunizing according to claim 8, wherein said nucleotide sequence encoding the conformational epitope comprising the VP1 neutralizing epitope of poliovirus type 2 comprises the nucleotide sequence of SEQ ID NO: 7.

12. The method for immunizing according to claim 8, wherein said nucleotide sequence encoding the conformational epitope comprising the VP1 neutralizing epitope of poliovirus type 3 comprises the nucleotide sequence of SEQ ID NO: 8.

13. The method for immunizing according to claim 8, wherein said recombinant Sabin type 1 poliovirus is a combination of (i) a recombinant Sabin type 1 poliovirus comprising the nucleotide sequence of the conformational epitope encoding the VP1 neutralizing epitope of poliovirus type 2; and (ii) a recombinant Sabin type 1 poliovirus comprising the nucleotide sequence of the conformational epitope encoding the VP1 neutralizing epitope of poliovirus type 3.

14. The method for immunizing according to claim 13, wherein said method further comprises boosting the individual by administering into the individual inactivated Sabin type 1, 2 and 3 polioviruses.

15. The method for immunizing according to claim 13, wherein said method further comprises boosting the individual by administering into the individual inactivated Sabin type 2 and 3 polioviruses.

* * * * *